United States Patent
Hanashi

(10) Patent No.: US 9,188,535 B2
(45) Date of Patent: Nov. 17, 2015

(54) SINGLE PARTICLE DETECTION DEVICE, SINGLE PARTICLE DETECTION METHOD, AND COMPUTER PROGRAM FOR SINGLE PARTICLE DETECTION, USING OPTICAL ANALYSIS

(71) Applicant: OLYMPUS CORPORATION, Tokyo (JP)

(72) Inventor: Takuya Hanashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/496,177

(22) Filed: Sep. 25, 2014

(65) Prior Publication Data

US 2015/0108369 A1 Apr. 23, 2015

Related U.S. Application Data

(63) Continuation of application No. PCT/JP2013/056600, filed on Mar. 11, 2013.

(30) Foreign Application Priority Data

Apr. 18, 2012 (JP) ................................. 2012-094503

(51) Int. Cl.
*G01N 21/64* (2006.01)
*G01N 15/14* (2006.01)

(52) U.S. Cl.
CPC ............ *G01N 21/64* (2013.01); *G01N 15/1434* (2013.01); *G01N 2201/06113* (2013.01)

(58) Field of Classification Search
CPC G01N 21/64; G01N 21/6452; G01N 21/6458
USPC .......................................... 250/458.1, 459.1
See application file for complete search history.

(56) References Cited

U.S. PATENT DOCUMENTS

| 4,251,733 A | 2/1981 | Hirleman, Jr. |
| 5,308,990 A | 5/1994 | Takahashi et al. |

(Continued)

FOREIGN PATENT DOCUMENTS

| EP | 1 906 172 A1 | 4/2008 |
| EP | 2840381 A1 | 2/2015 |

(Continued)

OTHER PUBLICATIONS

English translation of Written Opinion by ISA of International Application No. PCT/JP2013/056600 (Form PCT/ISA/237) mailed Jun. 18, 2013 with ISR (Form PCT/ISA/210) (6 pages).

(Continued)

*Primary Examiner* — Mark R Gaworecki
(74) *Attorney, Agent, or Firm* — Westerman, Hattori, Daniels & Adrian, LLP

(57) ABSTRACT

There is provided a single particle detection technique based on the scanning molecule counting method which individually detects single particles using light measurement with a confocal or multiphoton microscope, where the existences of a non-light-emitting particle and a light-emitting particle can be detected while being discriminated from one another in a sample solution. The inventive technique of detecting a single particle detects light from a light detection region during moving the position of the light detection region of the microscope in a sample solution containing a non-light-emitting particle and a light-emitting particle to generate time series light intensity data; and detects in the time series light intensity data a light intensity increase relative to background light intensity as a signal indicating the existence of the light-emitting particle and a light intensity reduction relative to the background light intensity as a signal indicating the existence of the non-light-emitting particle.

12 Claims, 9 Drawing Sheets

(56) References Cited

U.S. PATENT DOCUMENTS

| | | |
|---|---|---|
| 5,319,575 A | 6/1994 | Lilienfeld |
| 5,866,336 A | 2/1999 | Nazarenko et al. |
| 6,280,960 B1 | 8/2001 | Carr |
| 6,376,843 B1 | 4/2002 | Palo |
| 6,388,746 B1 | 5/2002 | Eriksson et al. |
| 6,388,788 B1 | 5/2002 | Harris et al. |
| 6,400,487 B1 | 6/2002 | Harris et al. |
| 6,403,338 B1 | 6/2002 | Knapp et al. |
| 6,710,871 B1 | 3/2004 | Goix |
| 6,856,391 B2 | 2/2005 | Garab et al. |
| 6,927,401 B1 | 8/2005 | Palo |
| 8,284,484 B2 | 10/2012 | Hoult et al. |
| 9,068,944 B2 | 6/2015 | Tanabe |
| 2001/0035954 A1 | 11/2001 | Rahn et al. |
| 2002/0008211 A1 | 1/2002 | Kask |
| 2002/0036775 A1 | 3/2002 | Wolleschensky et al. |
| 2003/0036855 A1 | 2/2003 | Harris et al. |
| 2003/0218746 A1 | 11/2003 | Sampas |
| 2004/0022684 A1 | 2/2004 | Heinze et al. |
| 2004/0051051 A1 | 3/2004 | Kato et al. |
| 2004/0150880 A1 | 8/2004 | Nakata et al. |
| 2005/0130122 A1 | 6/2005 | Aravanis et al. |
| 2005/0260660 A1 | 11/2005 | van Dongen et al. |
| 2006/0078998 A1 | 4/2006 | Puskas et al. |
| 2006/0158721 A1 | 7/2006 | Nakata et al. |
| 2006/0256338 A1 | 11/2006 | Gratton et al. |
| 2008/0052009 A1 | 2/2008 | Chiu et al. |
| 2008/0067133 A1 | 3/2008 | Bryant et al. |
| 2008/0158561 A1 | 7/2008 | Vacca et al. |
| 2009/0159812 A1 | 6/2009 | Livingston |
| 2010/0033718 A1 | 2/2010 | Tanaami |
| 2010/0177190 A1 | 7/2010 | Chiang et al. |
| 2010/0202043 A1 | 8/2010 | Ujike |

FOREIGN PATENT DOCUMENTS

| | | |
|---|---|---|
| JP | 04337446 A | 11/1992 |
| JP | 2002-507762 A | 3/2002 |
| JP | 2002-318188 A | 10/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2007-020565 A | 2/2007 |
| JP | 4023523 B2 | 12/2007 |
| JP | 2008-116440 A | 5/2008 |
| JP | 2008-523376 A | 7/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-002415 A | 1/2011 |
| JP | 2011-508219 A | 3/2011 |
| WO | 98/16814 A1 | 4/1998 |
| WO | 99/47963 A | 9/1999 |
| WO | 00/66985 A1 | 11/2000 |
| WO | 00/71991 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2010/119098 A1 | 10/2010 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |
| WO | 2012/039352 A1 | 3/2012 |
| WO | 2013/031309 A1 | 3/2013 |

OTHER PUBLICATIONS

Extended European Search Report dated Oct. 20, 2014, issued in related EP Application No. 12770835.2 (10 pages).

Park, Mira et al., "Counting the Number of Fluorophores Labeled in Biomolecules by Observing the Fluorescence-Intensity Transient of a Single Molecule", Bulletin of the Chemical Society of Japan, Aug. 30, 2005, vol. 78, No. 9, p. 1612-1618.

U.S. OFfice Action dated Apr. 2, 2013 issued in related U.S. Appl. No. 13/596,280 (7 pages).

Kask, Peet et al., "Two-Dimensional Fluorescence Intensity Distribution Analysis: Theory and Applications", Biophysical Journal, Apr. 2000, vol. 78, p. 1703-1713.

Chinese Office Action dated Aug. 13, 2013, issued in related Chinese application No. 201180011655.3; w/ English Translation (16 pages).

International Search Report dated Mar. 29, 2011, issued in related PCT/JP2011/053483.

Chinese Office Action dated Aug. 9, 2013, issued in related Chinese application No. 201180011640.7; w/ English Translation (16 pages).

International Search Report Mar. 29, 2011, issued in related PCT/JP2011/053482.

U.S. Office Action dated Jan. 3, 2013, issued in related U.S. Appl. No. 13/597,825 (5 pages).

Chinese Office Action dated Feb. 7, 2013, issued in related Chinese application No. 201180011644.5; w/ English Translation (19 pages).

Extended European Search Report dated Mar. 28, 2013, issued in related EP application No. 11750481.1.

Goodwin, Peter et al., "Rapid Sizing of Individual Fluorescently Stained DNA Fragments by Flow Cytometry", Nucleic Acids Research, 1993, vol. 21, No. 4, p. 803-806.

Keller, Richard et al., "Single-Molecule Fluorescence Analysis in Solution", Applied Spectroscopy, 1996, vol. 50, No. 7, p. 12A-32A.

Lee, Yuan-Hsiang et al., "Laser-Induced Fluorescence Detection of a Single Molecule in a Capillary", Analytical Chemistry, Dec. 1, 1994, vol. 66, No. 23, p. 4142-4149.

Li, Haitao et al., "Ultrasensitive Coincidence Fluorescence Detection of Single DNA Molecules", Analytical Chemistry, Apr. 1, 2003, vol. 75, No. 7, p. 1664-1670.

Nie, Shuming et al., "Probing Individual Molecules with Confocal Fluorescence Microscopy", Science, Nov. 11, 1994, vol. 266, p. 1018-1021.

Tahari, Abdel. "Fluorescence Correlation Spectroscopy: Ultrasensitive Detection in Clear and Turbid Media", University of Illinois, 2006, p. 1-88.

Wu, Alan et al., "Development and Preliminary Clinical Validation of a High Sensitivity Assay for Cardiac Troponin Using a Capillary Flow (Single Molecule) Fluorescence Detector", Clinical Chemistry, 2006, vol. 52, No. 11, p. 2157-2159.

Itoh et al., "A New Method for Detection of Influenza Viruses by Single Particle-Recognition Based on the Principle of Fluorescence Correlation Spectroscopy", Chemistry and Biology, 2009, vol. 47, No. 12, p. 823-830.

Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.

U.S. Office Action dated Oct. 4, 2013, issued in related U.S. Appl. No. 13/596,243 (7 pages).

Japanese Office Action dated Dec. 18, 2012, issued in related JP application No. 2012-503060; w/ English Translation (6 pages).

International Search Report dated Apr. 16, 2013, issued in related PCT/JP2013/050025.

U.S. Notice of Allowance dated Mar. 27, 2013, issued in related U.S. Appl. No. 13/597,825 (8 pages).

International Search Report dated Nov. 29, 2011, issued in related PCT/JP2011/072939.

Kask, Peet et al. "Fluorescence-Intensity Distribution Analysis and its Application in Biomolecular Detection Technology", PNAS, Nov. 23, 1999, vol. 96, No. 24, p. 13756-13761.

Kinjo, M. "Single Molecule Detection by Fluorescence Correlation Spectroscopy", Proteins, Nucleic Acids and Enzymes, 1999, vol. 44, No. 9, p. 1431-1438.

Meyer-Almes, F. J. "A New Method for Use in Molecular Diagnostics and High Throughput Pharmaceutical Screening based on Fluo-

(56) References Cited

OTHER PUBLICATIONS rescence Correlation Spectroscopy", Nanoparticle Immunoassays, R. Ridger, edit., Springer, Berlin, 2000, p. 204-224.
Kato, N. et al., "A Single Molecule Analyzer that Enables New Analysis of DNA and Protein Interactions", Gene & Medicine, 2002, vol. 6, No. 2, p. 271-277.
International Search Report dated May 7, 2013, issued in related PCT/JP2013/052110.
International Search Report dated Oct. 15, 2013, issued in related PCT/JP2013/068406.
International Search Report dated Jul. 24, 2012, issued in related PCT/JP2012/063139.
Related co-pending U.S. Appl. No. 14/465,208.
Related co-pending U.S. Appl. No. 14/162,142.
International Preliminary Report on Patentability (PCT/IPEA/409) dated Mar. 30, 2012, issued in related PCT/JP2011/053483.
International Preliminary Report on Patentability (PCT/IPEA/409) dated Mar. 30, 2012, issued in related PCT/JP2011/053482.
International Search Report dated Mar. 29, 2011, issued in related PCT/JP2011/053481.
International Preliminary Report on Patentability (PCT/IPEA/409) dated Jun. 15, 2012, issued in related PCT/JP2011/053481.
Supplementary European Search Report dated Apr. 23, 2015, issued in related European Patent Application No. 12828640. (16 pages).
Office Action dated Jun. 1, 2015, issued in Chinese Patent Application No. 201280041717.X w/English translation (26 pages).
Non-Final Office Action dated Aug. 4, 2015, issued in U.S. Appl. No. 14/162,142 (41 pages).

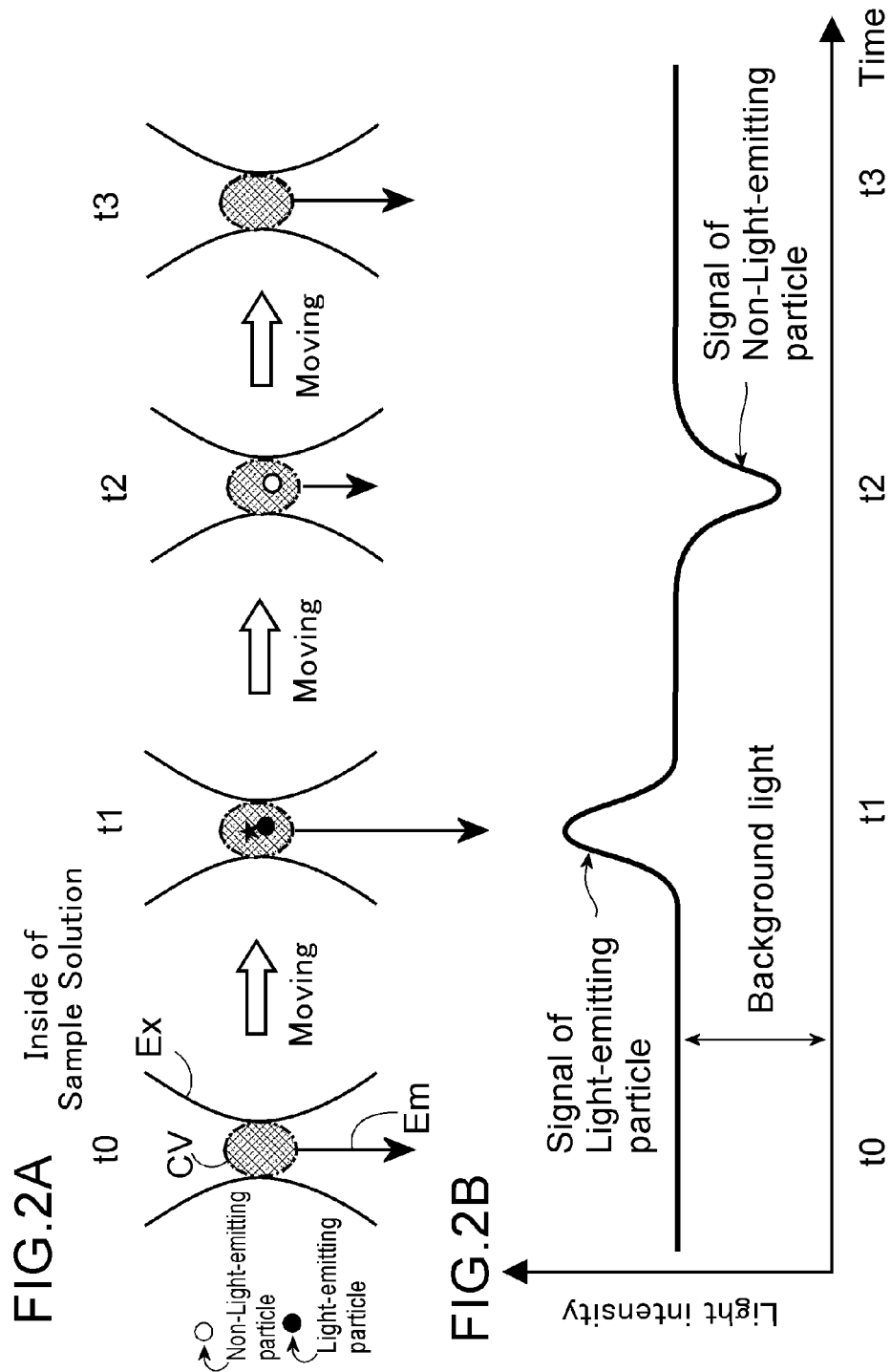

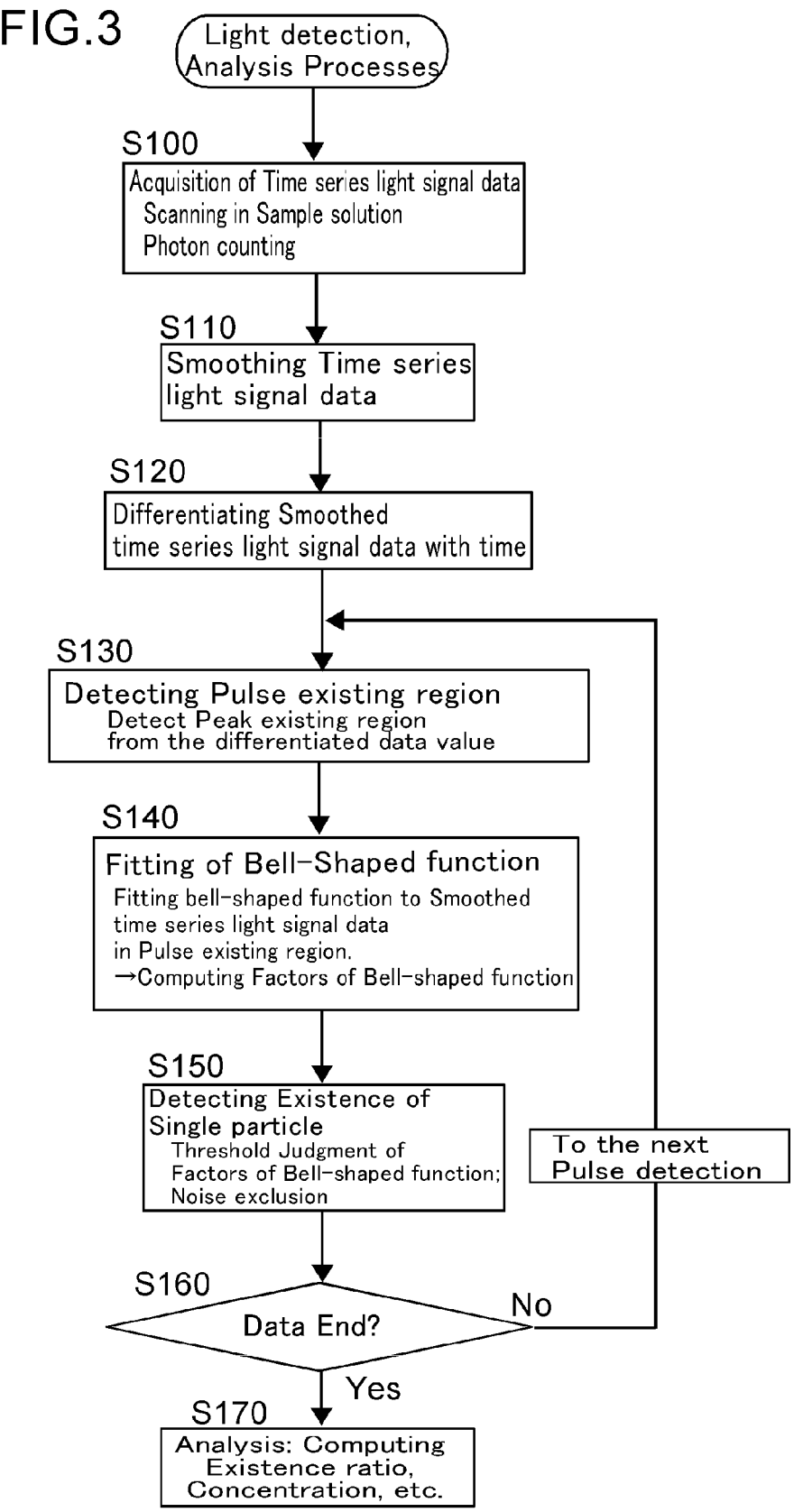

FIG.4A
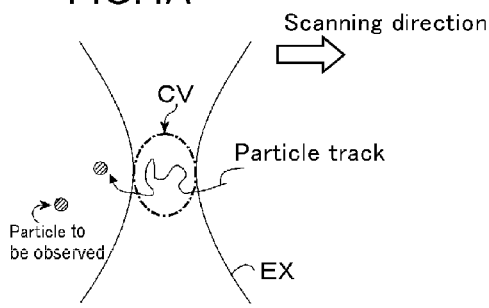
FIG.4B
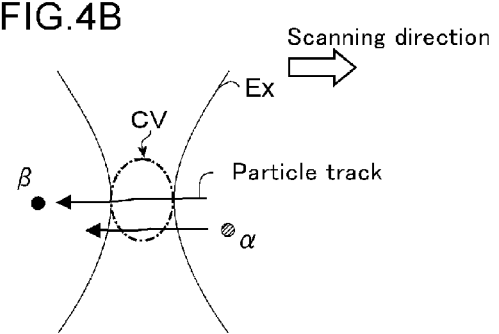
FIG.4C
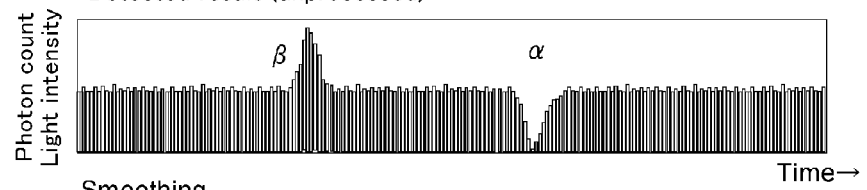
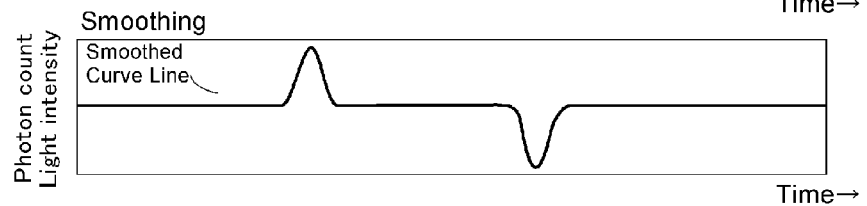
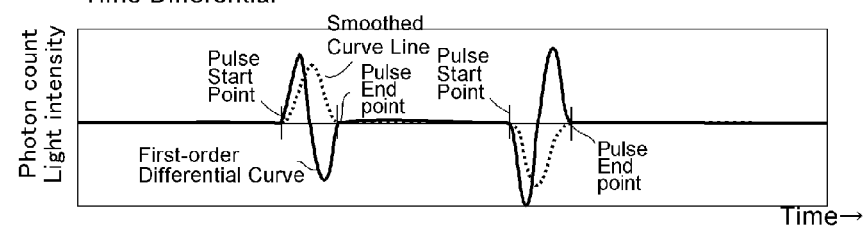
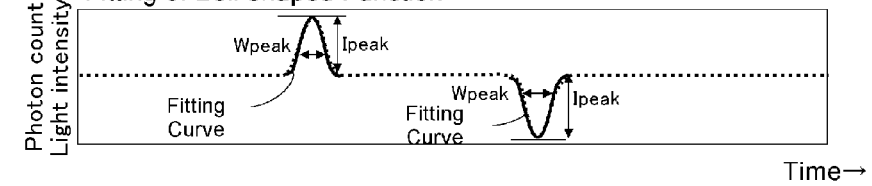

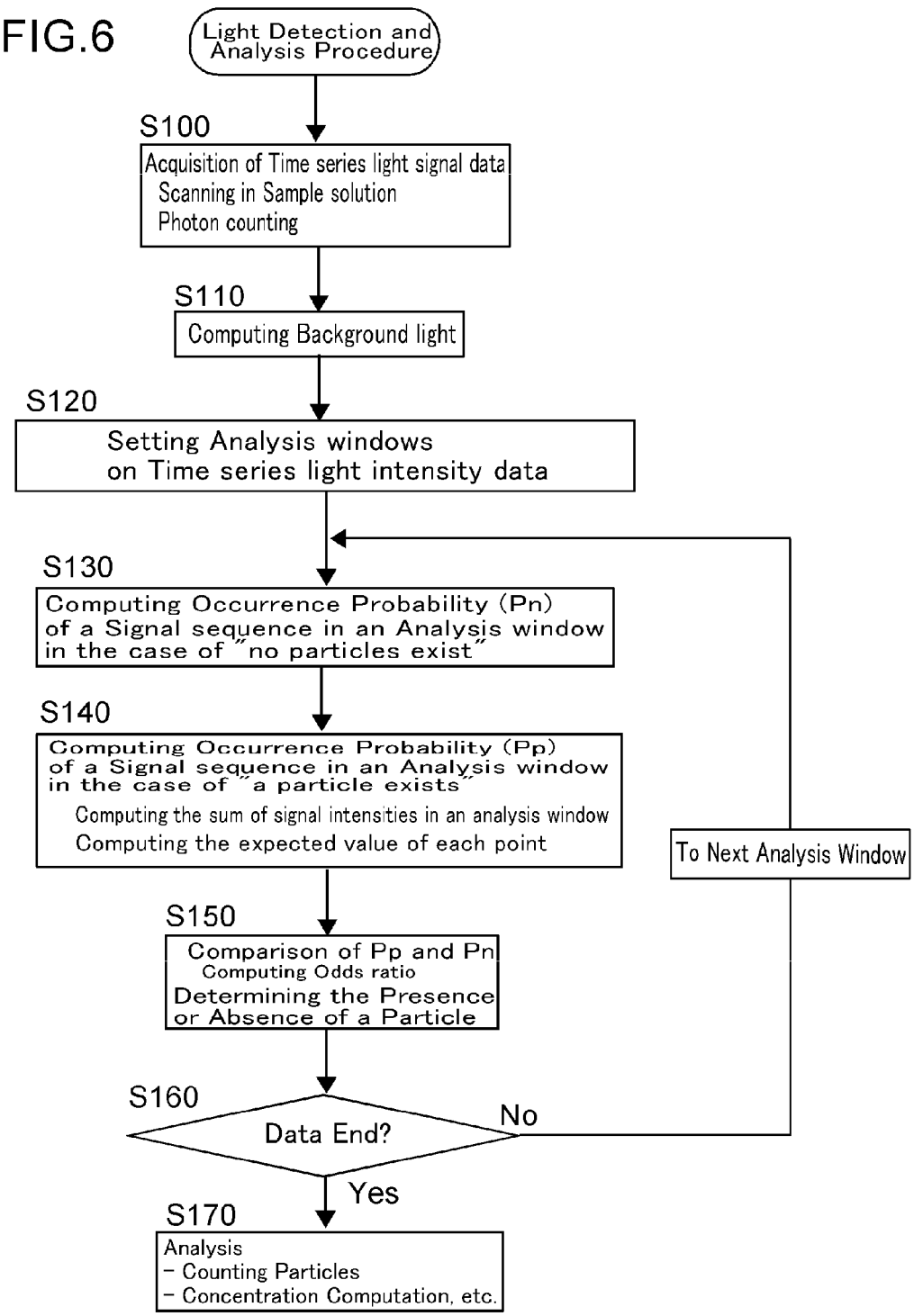

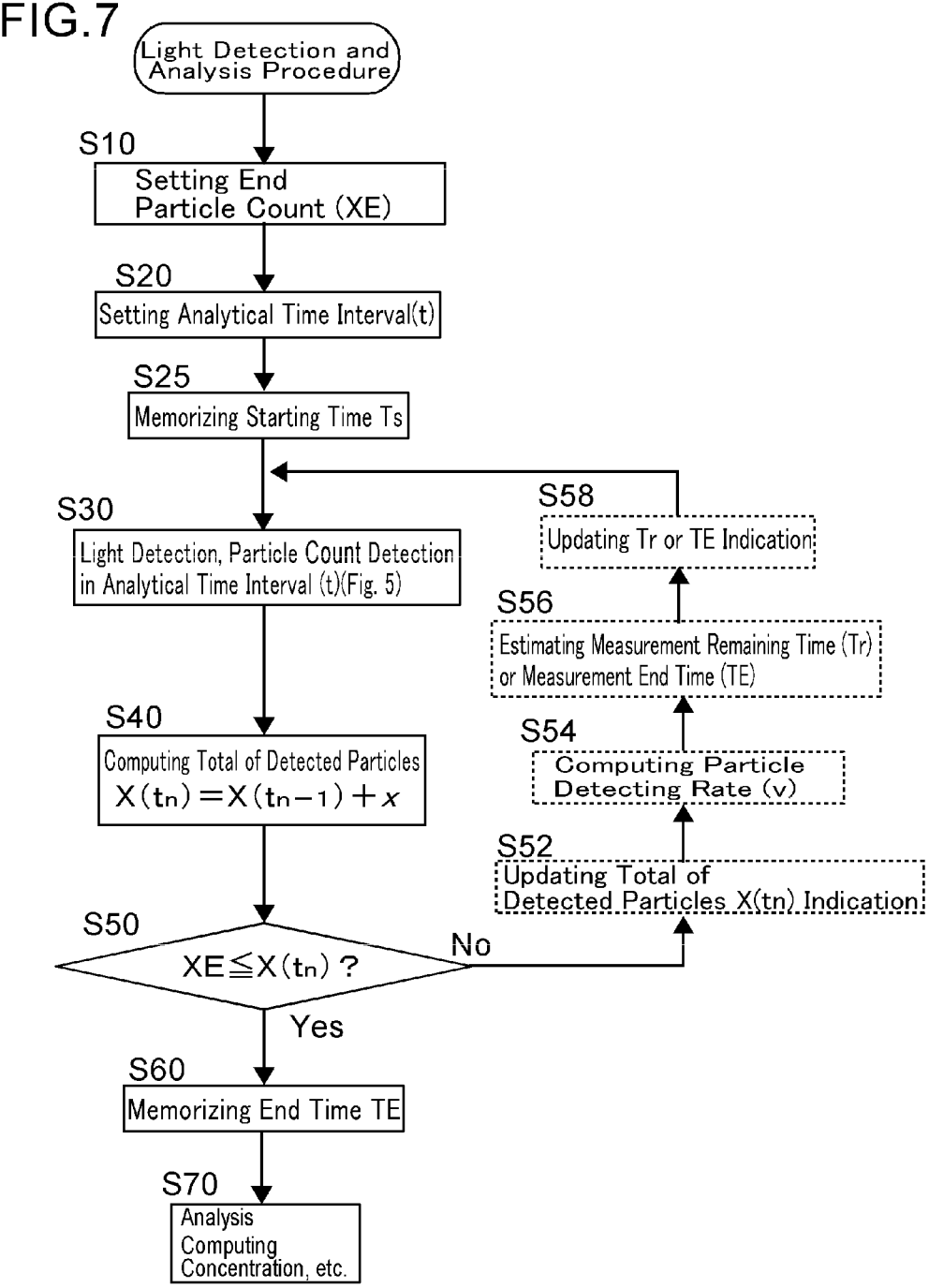

SINGLE PARTICLE DETECTION DEVICE, SINGLE PARTICLE DETECTION METHOD, AND COMPUTER PROGRAM FOR SINGLE PARTICLE DETECTION, USING OPTICAL ANALYSIS

TECHNICAL FIELD

This invention relates to a single particle detection technique capable of detecting a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (interaction, binding or dissociating condition, etc.) of particles, and more specifically, relates to a single particle detection device, a single particle detection method and a computer program for single particle detection, measuring with an optical system as described above a light intensity variation because of an existence of a single particle to detect a single particle, and thereby enabling various analyses.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed optical analysis techniques of performing detection of a characteristic, an intermolecular interaction, a binding or dissociating reaction of a biological molecule, etc. by means of such a faint light measurement technique. As such optical analysis techniques, for example, there are known Fluorescence Correlation Spectroscopy (FCS, see e.g. patent documents 1-3 and non-patent documents 1-3), Fluorescence Intensity Distribution Analysis (FIDA, e.g. patent document 4, non-patent document 4) and Photon Counting Histogram (PCH, e.g. patent document 5). In addition, in patent documents 6-8, there are proposed methods of detecting fluorescent substances based on a time progress of fluorescence signals of a sample solution measured using the optical system of a confocal microscope.

Furthermore, in patent documents 9-11, Applicant of the present application has proposed a novel optical analysis technique, using an optical system which is capable of detecting the light from a micro region in a solution, such as an optical system of a confocal microscope or a multiphoton microscope, and employing a different principle from optical analysis techniques, such as FCS and FIDA. In the case of optical analysis techniques, such as the above-mentioned FCS, FIDA, briefly speaking, there are conducted statistical calculation processes for the light intensity data obtained by continuously measuring lights from fluorescence molecules floating in a micro region, in which light is detected, in a sample solution (hereafter, called a "light detection region"), and thereby a concentration and/or other characteristics of fluorescence molecules are detected. On the other hand, in the new optical analysis technique proposed in patent documents 9-11, the position of a light detection region is moved in a sample solution (i.e., the inside of the sample solution is scanned with the light detection region), and when the light detection region encompasses a particle which emits light (a light-emitting particle) being dispersed and moving at random in the sample solution, the light emitted from the light-emitting particle is individually detected, and thereby each of the light-emitting particles in the sample solution is detected individually so that it becomes possible to perform the counting of light-emitting particles and the acquisition of the information about the concentration or number density of the light-emitting particle in the sample solution. According to this optical analysis technique (called the "scanning molecule counting method", hereafter.), not only the sample amount necessary for measurement may be very small (for example, about several 10 μL) and the measuring time is short similarly to optical analysis techniques, such as FCS and FIDA, but also, it becomes possible to detect the presence of a light-emitting particle and quantitatively detect its characteristic, such as a concentration, a number density, etc., at a lower concentration or number density, as compared with the cases of optical analysis techniques, such as FCS and FIDA. Thus, the "scanning molecule counting method" is expected to be a strong tool enabling an experiment or a test at low cost and/or more quickly than conventional biochemical methods, and also enabling the detection of a concentration and/or a characteristic of a particle of a lower concentration at which FCS, FIDA, etc. cannot be acceptably performed, especially in conducting an analysis of a rare or expensive sample often used in the field of the medical or biological research and development or in conducting tests of a large number of specimens, such as sick clinical diagnosis or the screening of bioactive substances.

PRIOR TECHNICAL DOCUMENTS

Patent documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446
Patent document 9: WO2011/108369
Patent document 10: WO2011/108370
Patent document 11: WO2011/108371
Patent document 12: WO2010/119098

Non-Patent Documents

Non-patent document 1: Masataka Kinjo; "Protein, Nucleic acid, Enzyme" Vol. 44, No. 9, pages 1431-1438, 1999.
Non-patent document 2: F. J. Meyer-Alms; "Fluorescence Correlation Spectroscopy" edt. R. Rigler, Springer, Berlin, pages 204-224, 2000.
Non-patent document 3: Noriko Kato, et al. "Gene medicine", Vol. 6, No. 2, pages 271-277.
Non-patent document 4: P. Kask, K. Palo, D. Ullmann, K. Gall PNAS 96, 13756-13761 (1999)

SUMMARY OF INVENTION

Technical Problem

By the way, in the case of the optical system of a confocal microscope or a multiphoton microscope used in the scanning molecule counting method as described above, the resolution in the direction of the optical axis is higher than usual light microscopes, and therefore, in a case where significant background light is emitted from the confocal volume (light detection region), if a single particle which does not emit light passes through the inside of the confocal volume, a reduction of the light intensity from the confocal volume is observed (patent document 12). Then, in the Japanese patent application No. 2011-184635, Applicant of the present application has proposed "Inverted scanning molecule counting method", which detects the existence of a single particle by performing light detection by scanning the inside of a sample solution which emits substantially constant background light with a light detection region in a manner similar to the "scanning molecule counting method" while a single particle which emits no light is employed as a particle to be observed, and detecting a reduction of the light intensity owing to the single particle which emits no light or of which emitted light intensity is lower than the background light when it is encompassed in the inside of the light detection region. According to this "inverted scanning molecule counting method", it becomes possible to detect a single particle which emits no light at a low concentration.

In addition, according to researches of the inventor of the present invention, etc., it has been found that, even in the presence of significant background light in the light from a confocal volume as in the case of the above-mentioned "inverted scanning molecule counting method", if the emitted light intensity from a light-emitting particle is higher than the background light, the light emitted by a single light-emitting particle is detectable individually. Accordingly, in a solution containing a single particle which emits no light or has a light intensity lower than the background light in a detected light wavelength (hereafter, referred to as a "non-light-emitting particle") and a single light-emitting particle whose emitted light intensity is higher than the background light in the detected light wavelength, when the light measurement is performed in accordance with the scanning molecule counting method, a signal corresponding to a non-light-emitting particle (a light intensity variation) will appear convex downwardly and a signal corresponding to a light-emitting particle will appear convex upwardly. Namely, in this case, it becomes possible to detect the individual existences of the non-light-emitting particle and light-emitting particle contained in the same sample solution simultaneously while distinguishing between them mutually. In the present invention, this knowledge will be used advantageously.

Thus, the main object of the present invention is to provide a single particle detection technique which makes it possible to detect and identify individually the presences of a single particle which emits no light or has a light intensity lower than the background light in a detected light wavelength ("non-light-emitting particle") and a single light-emitting particle whose emitted light intensity is higher than the background light in the detected light wavelength ("light-emitting particle") in a case that the non-light-emitting particle and the light-emitting particle are contained in the same solution.

Solution to Problem

According to one aspect of the present invention, the above-mentioned object is achieved by a single particle detection device which detects single particles dispersed and moving at random in a sample solution using an optical system of a confocal microscope or a multiphoton microscope, comprising: a light detection region mover which moves a position of a light detection region of the optical system of the microscope in the sample solution; a light detector which detects light from the light detection region; and a signal processor which generates time series light intensity data of the light from the light detection region detected with the light detector during the moving of the position of the light detection region in the sample solution and detects a signal indicating an existence of each single particle individually in the time series light intensity data; wherein the light from the light detection region detected by the light detector includes substantially constant background light; single particles comprises a first single particle having an emitted light intensity higher than the background light and a second single particle having an emitted light intensity lower than the background light; a signal of the first single particle is an increase of the light intensity detected in the light detector when the first single particle enters into the light detection region and a signal of the second single particle is a reduction of the light intensity detected in the light detector when the second single particle enters into the light detection region.

In this structure, "single particles dispersed and moving at random in a sample solution" may be arbitrary particulate matters, such as atoms, molecules or aggregates of these, dispersed or dissolved in a sample solution, making the Brownian motion freely in the solution without being fixed on a substrate, etc. The "light detection region" of the optical system of the confocal microscope or multiphoton microscope is the micro region where light is detected in those microscopes, which region corresponds to the region to which illumination light is condensed when the illumination light is given from an objective (Especially in the confocal microscope, this region is determined in accordance with the spatial relationship of an objective and a pinhole.). "the light from the light detection region . . . includes substantially constant background light" means that the intensity value of the detected light (namely, the background light) in the absence of single particles to be observed in the inside of the light detection region is a significant intensity value within an allowable error range. In other words, the background light is adjusted so that its variation may become smaller enough than the width of the intensity variation of the detected light generated when a single particle enters into the light detection region. In this regard, in this specification, "a signal of a single particle" indicates a signal indicating the existence of a single particle unless noted otherwise. "detects a signal indicating an existence of each single particle individually" is intended to mean to detect a temporary increase or reduction of light intensity on time series light intensity data which is generated when a single particle enters to the inside of the light detection region one by one for each single particle. Further, in the following, a single particle which has an emitted light intensity higher than the background light (the first single particle) is referred to as a "light-emitting particle"; and a single particle which has an emitted light intensity lower than the background light (the second single particle) is referred to as a "non-light-emitting particle". Namely, for the non-light-emitting particle, although it is preferable that its emitted light intensity in the wavelength band of the detected light is almost zero, the level significantly lower than the background light intensity may be allowed.

As understood from the above, in the inventive device, basically, similarly to the "scanning molecule counting method" described in the patent documents 9-11, the detection of light and the generation of the time series light intensity data indicating time series light intensity values are sequentially performed during moving the position of the light detection region in the sample solution, namely, during scanning the inside of the sample solution with the light detection region. In this structure, in a case that background light of significant intensity is included in the light from the light detection region, when a light-emitting particle (the first single particle) enters into the light detection region or when the light detection region moving within the sample solution encompasses a light-emitting particle, the light intensity or the light amount reaching from the light detection region to the light detector increases due to the existence of the light-emitting particle, and when a non-light-emitting particle (the second single particle) enters into the light detection region or when the light detection region moving within the sample solution encompasses a non-light-emitting particle, the light intensity or the light amount which reaching from the light detection region to the light detector reduces due to the existence of the non-light-emitting particle. Thus, in the inventive device, in a case that a light-emitting particle and a non-light-emitting particle are contained in a sample solution for single particles to be observed, the light detection is performed under a condition that significant background light intensity (of which value is lower than the light intensity of the light-emitting particle and higher than the light intensity of the non-light-emitting particle) from the light detection region can be detected, and time series light intensity data is generated. Then, by detecting an increase and/or a reduction in the light intensity or the light amount individually in the time series light intensity data as signals of the first and second single particles, respectively, the existences of the first and second single particles will be detected while being mutually distinguished. According to this structure, mutually different particles, i.e., the first, and the second particles, in a sample solution will be detected separately from one another, namely, by the kind, and thus, diverse information about conditions within a solution of particles will be acquired for each kind. In other words, in the inventive device, in the light measurement in a certain detected wavelength band, it is possible to detect individually single particles of at least two mutually different kinds.

In the above-mentioned inventive device, the background light to be included in the light from the light detection region may be fluorescence, phosphorescence, chemiluminescence, bioluminescence or scattered light by substance dispersed in the sample solution. In this case, when no substance emitting or scattering light is dispersed in a solution used as a sample solution, substance emitting or scattering light may be dissolved or dispersed into this solution positively. Further, when a solution used as a sample solution emits autofluorescence, the autofluorescence may be used as the above-mentioned background light. Especially when substance producing background light and a light-emitting particle to be a particle to be observed needs excitation light or illumination light, the microscope device is equipped with a light source and an optical system for the illumination light. On the other hand, in a case that substance producing background light emits light without excitation light or illumination light, for example, in a case of substance emitting light according to chemiluminescence or bioluminescence, no illumination light is required in the microscope device. Furthermore, it should be understood that the background light may be illumination light by transmitted illumination, etc. if it is reduced when a non-light emitting particle exists in the light detection region.

Further, in the relation between the emitted light intensity of a light-emitting particle and background light intensity in the above-mentioned inventive device, it is preferable that the emitted light intensity of a light-emitting particle is sufficiently large to be discriminated from the background light intensity. For this, preferably, the relation between the emitted light intensity of a light-emitting particle and the background light intensity will be adjusted so that the emitted light intensity of a light-emitting particle will be higher than the background light intensity emitted from the volume region equivalent to the volume excluded when the light-emitting particle exists in the light detection region. Namely, it is preferable that the background light intensity and the emitted light intensity of a light-emitting particle are so adjusted that the emitted light intensity emitted from the light-emitting particle (the first single particle) per unit volume will exceed beyond the background light intensity emitted from the inside of the light detection region per unit volume. On the other hand, in the relation between the emitted light intensity of a non-light-emitting particle and the background light intensity in the inventive device, if the relation between the emitted light intensity of a non-light-emitting particle and the background light intensity is so adjusted that the emitted light intensity of a non-light-emitting particle will be lower than the background light intensity emitted from the volume region equivalent to the volume excluded when the non-light-emitting particle exists in the light detection region, the reduction of the light intensity due to the existence of the non-light-emitting particle occurs. Thus, it is preferable that the background light intensity and the emitted light intensity of a non-light-emitting particle are adjusted so that the emitted light intensity emitted from the non-light-emitting particle (the second single particle) per unit volume will be lower than the background light intensity emitted from the inside of the light detection region per unit volume. Especially, in a case of the detection of reduction of the background light due to the existence of a non-light-emitting particle, the degree of the reduction of the background light is dependent on the relation between the size of the non-light-emitting particle and the size of the light detection region. In this respect, according to the estimation in consideration of the width of variation of the background light as described later, it has been found that, when the emitted light intensity of a non-light-emitting particle is substantially 0, it is preferable that the outer diameter of a non-light-emitting particle be not less than 15% of the diameter of a light detection region, and it is more preferable that the outer diameter of a non-light-emitting particle be not less than 35% of the diameter of the light detection region. (see Japanese Patent Application No. 2011-184635). In the case of the light-emitting particle, the brighter the emitted light intensity per unit volume is, the smaller the ratio of the detectable outer diameter of the light-emitting particle to the diameter of the light detection region is. For instance, the adjustment of the background light may be done by adjusting the amount of arbitrary light-emitting substance dispersed in the sample solution.

In the above-mentioned inventive device, the moving speed of the position of the light detection region in the sample solution may be appropriately changed based on the characteristics, number density or concentration of the single particle in the sample solution. Especially when the moving speed of the light detection region becomes quick, the degree of increase/reduction of the light intensity or light amount because of the existence of a single particle will decrease, and thus, in order to make it possible to precisely and sensitively measure an increase/a reduction of the light intensity or light amount because of a single particle, it is preferable that the moving speed of the light detection region is changeable appropriately.

Furthermore, the moving speed of the position of the light detection region in the sample solution is preferably set to be higher than the diffusional moving velocity of a single particle to be a detected object (the average moving speed of a particle owing to the Brownian motion). As explained above, in the inventive device, a single particle will be detected individually by detecting an increase/a reduction of light intensity or light amount because of the existence of the single particle when the light detection region passes through the existence position of the single particle. However, when the single particle moves at random owing to the Brownian motion to move into and out of the light detection region multiple times, it is possible that the signal from one single particle showing its existence will be detected multiple times, and therefore it would become difficult to make the existence of one single particle associated with the detected signal. Then, as described above, the moving speed of the light detection region is set higher than the diffusional moving velocity of a single particle, and thereby it becomes possible to make one light-emitting particle correspond to one signal (indicating the single particle). In this regard, since the diffusional moving velocities differ depending upon characteristics of single particles, preferably, the inventive device is so designed that the moving speed of the light detection region can be changed appropriately according to the characteristics (especially, the diffusion constant) of the single particle as described above.

The moving of the position of the light detection region may be done in an arbitrary way. For example, the position of the light detection region may be changed by changing the optical path, such as by using a galvanomirror employed in a laser scan type optical microscope, or the relative position of the light detection region in the sample solution may be moved by moving the position of the sample solution, such as by moving the stage of the microscope. The movement track of the position of the light detection region may be set arbitrarily, for example, which is selectable from circular, elliptical, rectangular, straight and curvilinear ones. Especially, in the case that the position of the light detection region is moved by changing the optical path of the optical system of the microscope, it is advantageous in that the movement of the light detection region is quick without substantial generation of mechanical vibration and hydrodynamic effect in the sample solution, and therefore, the measurement of light can be performed under a stable condition without dynamic action affecting the single particle to be an object to be detected in the sample solution.

Moreover, in the process of the signal processor of the above-mentioned inventive device, the judgment of whether or not one particle has entered into the light detection region by means of signals of successive detected values from the light detector may be done based on the shape of time series signals indicating light detected in the light detector. In one of embodiments, when a signal whose light intensity is higher or lower than a predetermined threshold value measured from the background light intensity is detected, it may be judged that one single particle has entered into the light detection region. More concretely, as explained in the column of the embodiments later, usually, in the detected time series values of a light detector, i.e., light intensity data, a signal indicating the existence of a single particle appears as upwardly convex, bell-shaped pulse form signal exceeding beyond a certain degree of intensity (in the case of a light-emitting particle) or as a downwardly convex, bell-shaped pulse form signal descending below a certain degree of intensity (in the case of a non-light-emitting particle), and a noise appears in non bell-shaped pulse form or as a signal with a small amplitude. Then, the signal processor of the inventive device may be designed to detect a upwardly convex, pulse form bell shaped signal ascending beyond a predetermined threshold value or a downwardly convex, pulse form bell shaped signal descending below a predetermined threshold value, measured from a background light intensity as a signal indicating the existence of a single particle in time series light intensity data. The "predetermined threshold value" can be experimentally set to an adequate value.

Furthermore, the light intensity obtained by the inventive device is comparatively weak, in which there are generated minute increases and decreases, causing deterioration of the detection accuracy of a signal indicating the existence of a single particle. Thus, the signal processor may be designed to conduct the smoothing of the time series light intensity data for processing the data where minute increases and decreases in the light intensity can be disregarded, and then to detect in the smoothed time series light intensity data a upwardly convex bell-shaped pulse form signal ascending over a predetermined threshold value or a downwardly convex bell-shaped pulse form signal whose intensity descends below a predetermined threshold value, measured from the background light intensity, as a signal indicating the existence of a single particle.

Furthermore, in another embodiment, the process of detecting a signal of a single particle may be conducted in a manner that computes an occurrence probability in assuming the condition that no single particles exist in the light detection region and an occurrence probability in assuming the condition that a single particle exists in the light detection region for a time variation of the light intensity on light intensity data, and detects a signal indicating the existence of each single particle by detecting a time period in which a single particle existed in the light detection region based on those occurrence probabilities (see Japanese Patent Application No. 2012-32421). Briefly, it has been found that, in time series light intensity data of the scanning molecule counting method, while noises are always random and transient increase/reduction of light intensity, the signal of a single particle is a temporally concentrative increase/a reduction of the light intensity. Namely, the signal of a single particle and the noise are mutually different in the pattern of a time variation of light intensity value in time series light intensity data, and therefore, when the pattern of a time variation of light intensity value in a certain portion on time series light intensity data is a pattern which is prone to be generated in a case that no single particles exist in the light detection region, the portion can be judged as a portion of only noise, while, when the pattern in a certain portion is a pattern which is prone to be generated in a case that a single particle exists in the light detection region, the portion can be judged as a portion corresponding to a signal of a single particle. Thus, the detection of a signal of a single particle becomes possible by computing the probabilities for the pattern of a time variation of light intensity value appearing on time series light intensity data in the respective cases of the presence and absence of a single particle in the light detection region, and judging whether the pattern of the time variation of the light intensity value is prone to be generated in a case that a single particle exists in the light detection region or in a case that no single particles exist.

Moreover, in one of manners of the above-mentioned present invention, the number of single particles encompassed in the light detection region may be counted by counting the number of the selectively detected signals (The counting of particles). In that case, by associating the number of the detected single particles with the moving amount of the position of the light detection region, the information on the number density or concentration of the single particle identified in the sample solution will be acquired. Concretely, for instance, the ratio of number densities or concentrations of two or more sample solutions or a relative ratio of a number density or concentration to a standard sample solution to be the reference of a concentration or a number density may be computed, or an absolute number density value or concentration value may be determined using a relative ratio of a number density or concentration to a standard sample solution to be the reference of a concentration or a number density. Or, by determining the whole volume of the moving track of the position of the light detection region by an arbitrary method, for example, by moving the position of the light detection region at a predetermined speed, the number density or concentration of the single particle can be concretely computed. Especially in the case of the present invention, for light-emitting particles and non-light-emitting particles contained in the same sample solution, the counting of the respective numbers and/or the computation of the respective concentrations are possible separately.

In this connection, with respect to the counting of particles as described above, in its typical manner, the number of the signals of single particles obtained in the measuring time set arbitrarily is counted. In that case, however, the number of the detected signals of the single particles changes with the length of the set measuring time, and especially, in a case of a low single particle concentration, the scattering of the single particle concentration values computed from the numbers of detected signals becomes large, so that its accuracy would be reduced. Thus, in the above-mentioned inventive device, as another manner of the counting of particles, the measurement may be performed until the number of signals of single particles reaches an arbitrarily set number, and based on its measuring time, the single particle concentration value may be computed. Namely, the above-mentioned inventive device may be designed to repeat the moving of the position of the light detection region of the optical system by the light detection region mover, the detecting of the light from the light detection region by the light detector and the detecting of the signals indicating the existences of the single particle by the signal processor until the number of the signals indicating the existences of the single particles detected with the signal processor reaches a predetermined number; and to determine a concentration of the single particle in the sample solution based on the time taken for the number of the signals indicating the existences of the single particles to reach the predetermined number. In this case, the shortening of the measuring time for a sample solution of a high single particle concentration is expected, and the measurement for a sample solution of a low single particle concentration will be performed with spending sufficient time. That is, according to the above-mentioned structure, the measuring time is optimized in accordance with the single particle concentrations. Moreover, when the predetermined number is set to the number which attains the accuracy requested for the result, the scatterings in the time taken for the detection of the predetermined number of the single particles and an arbitrary result derived therefrom can be suppressed, and the accuracy of the result(s) can be made satisfactory.

The processes of the single particle detection technique of conducting the light detection in the presence of background light with moving the position of the light detection region in a sample solution containing a light-emitting particle and a non-light-emitting particle together, and successively detecting an increase or a reduction of the light intensity or light amount as a signal of a light-emitting particle or a non-light-emitting particle individually in the above-mentioned inventive device can be realized with a general-purpose computer, also. Thus, according to another aspect of the present invention, there is provided a computer readable storage device having a computer program product including programmed instructions for optical analysis of detecting light from a single particle dispersed and moving at random in a sample solution using an optical system of a confocal microscope or a multiphoton microscope, said programmed instructions causing a computer to perform steps comprising: moving a position of a light detection region of the optical system of the microscope in the sample solution; detecting light from the light detection region with moving the position of the light detection region in the sample solution, and generating time series light intensity data; and detecting a signal indicating an existence of each single particle individually in the time series light intensity data; wherein the detected light from the light detection region includes substantially constant background light; single particles comprises a first single particle having an emitted light intensity higher than the background light and a second single particle having an emitted light intensity lower than the background light; a signal of the first single particle is an increase of the light intensity detected in the light detector when the first single particle enters into the light detection region and a signal of the second single particle is a reduction of the light intensity detected in the light detector when the second single particle enters into the light detection region. In this regard, the computer program is provided while being memorized in a computer readable storage medium. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

Also in this structure, the background light may be fluorescence, phosphorescence, chemiluminescence, bioluminescence or scattered light owing to substance dispersed in the sample solution, or illumination light. Further, preferably, the background light intensity and the emitted light intensities of the light-emitting particle and the non-light-emitting particle are adjusted so that, in the relation between the emitted light intensity of the light-emitting particle and the background light intensity, the emitted light intensity emitted from the light-emitting particle (the first single particle) per unit volume will exceed beyond the background light intensity emitted from the inside of the light detection region per unit volume, and in the relation between the emitted light intensity of the non-light-emitting particle and the background light intensity, the emitted light intensity emitted from the non-light-emitting particle (the second single particle) per unit volume is lower than the background light intensity emitted from the inside of the light detection region per unit volume. Especially, it is preferable that the outer diameter of a non-light-emitting particle be not less than 15% of the diameters of a light detection region, and it is more preferable that the outer diameters of a non-light-emitting particle be not less than 35% of the diameters of the light detection region.

Moreover, even in the above-mentioned computer program, the individual detection of a signal indicating the existence of each single particle may be done based on the shape of the time series signal. In an embodiment, typically, in the step of detecting the signal indicating the existence of the single particle individually, it may be judged that one light-emitting particle has entered into the light detection region when a signal whose light intensity is higher than a predetermined threshold value measured from the intensity of the background light is detected and it may be judged that one non-light-emitting particle has entered into the light detection region when a signal whose light intensity is lower than a predetermined threshold value measured from the intensity of the background light is detected. Concretely, in the step of detecting the signal indicating the existence of the single particle individually, a upwardly convex, bell-shaped pulse form signal whose intensity is higher than a predetermined threshold value measured from the intensity of the background light in the time series light intensity data may be detected as the signal indicating the existence of the light-emitting particle, and a downwardly convex, bell-shaped pulse form signal whose intensity is lower than a predetermined threshold value measured from the intensity of the background light in the time series light intensity data may be detected as the signal indicating the existence of the single particle, and in this case, the time series light intensity data may be smoothed and a bell-shaped pulse form signal in the smoothed time series light intensity data may be detected as a signal indicating the existence of a single particle. Alternatively, in another manner of individual detection of signals indicating the respective existences of different single particles, the detection of a signal of a single particle may conducted by computing the probabilities for a pattern of the time variation of light intensity value appearing on time series light intensity data in the respective cases of the presence and absence of a single particle in the light detection region, and judging whether the pattern of the time variation of the light intensity value is prone to be generated in a case that a single particle exists in the light detection region or in a case that no single particles exist.

Furthermore, the moving speed of the position of the light detection region in the sample solution may be appropriately changed based on the characteristics, number density or concentration of the single particle in the sample solution, and preferably, the moving speed of the position of the light detection region in the sample solution is set higher than the diffusion moving velocity of the single particle to be an object to be detected. The moving of the position of the light detection region in the sample solution may be done by an arbitrary way, and preferably, the position of the light detection region may be changed by changing the optical path of the optical system of the microscope or by moving the position of the sample solution. The movement track of the position of the light detection region may be set arbitrarily, for example, which is selectable from circular, elliptical, rectangular, straight and curvilinear ones.

Further, the above-mentioned computer readable storage device may also comprise a step of counting a number of the signals indicating the existences of the single particles individually detected during moving the position of the light detection region to count a number of the single particles and/or a step of determining a number density or concentration of the single particle in the sample solution based on the number of the detected single particles. In this regard, also in the case of the above-mentioned computer readable storage device, typically, the counting of particles is conducted by counting the number of signals of single particles obtained in a arbitrarily set measuring time; however, the measurement may be performed until the number of signals of single particles reaches an arbitrarily set number, and the single particle concentration value may be computed based on the measuring time. Thus, the above-mentioned computer readable storage device may be designed to repeat the detecting of the light from the light detection region and the detecting of the signals indicating the existences of the single particle until the number of the signals indicating the existences of the single particles detected with the signal processor reaches a predetermined number the moving of the position of the light detection region of the optical system; and to determine a concentration of the single particle in the sample solution based on the time taken for the number of the signals indicating the existences of the single particles to reach the predetermined number.

According to the above-mentioned inventive device or computer readable storage device, there is realized a novel method of conducting the light detection in the presence of background light with moving the position of the light detection region in a sample solution containing a light-emitting particle and a non-light-emitting particle together, and successively detecting individually an increase or a reduction of the light intensity or light amount as a signal of the light-emitting particle and the non-light-emitting particle single particle, respectively. Thus, according to the present invention, there is further provided a single particle detection method of detecting single particles dispersed and moving at random in a sample solution using an optical system of a confocal microscope or a multiphoton microscope, comprising steps of: moving a position of a light detection region of the optical system of the microscope in the sample solution; detecting light from the light detection region with moving the position of the light detection region in the sample solution, and generating time series light intensity data; and detecting a signal indicating an existence of each single particle individually in the time series light intensity data; wherein the detected light from the light detection region includes substantially constant background light; single particles comprises a first single particle having an emitted light intensity higher than the background light and a second single particle having an emitted light intensity lower than the background light; a signal of the first single particle is an increase of the light intensity detected in the light detector when the first single particle enters into the light detection region and a signal of the second single particle is a reduction of the light intensity detected in the light detector when the second single particle enters into the light detection region.

Also in this structure, the background light may be fluorescence, phosphorescence, chemiluminescence, bioluminescence or scattered light owing to substance dispersed in the sample solution, or illumination light. Further, preferably, the background light intensity and the emitted light intensities of the light-emitting particle and the non-light-emitting particle are adjusted so that, in the relation between the emitted light intensity of the light-emitting particle and the background light intensity, the emitted light intensity emitted from the light-emitting particle (the first single particle) per unit volume will exceed beyond the background light intensity emitted from the inside of the light detection region per unit volume, and in the relation between the emitted light intensity of the non-light-emitting particle and the background light intensity, the emitted light intensity emitted from the non-light-emitting particle (the second single particle) per unit volume is lower than the background light intensity emitted from the inside of the light detection region per unit volume. Especially, it is preferable that the outer diameter of a non-light-emitting particle be not less than 15% of the diameters of a light detection region, and it is more preferable that the outer diameters of a non-light-emitting particle be not less than 35% of the diameters of the light detection region.

Moreover, even in the above-mentioned method, the individual detection of a signal indicating the existence of each single particle may be done based on the shape of the time series signal. In an embodiment, typically, in the step of detecting the signal indicating the existence of the single particle individually, it may be judged that one light-emitting particle has entered into the light detection region when a signal whose light intensity is higher than a predetermined threshold value measured from the intensity of the background light is detected and it may be judged that one non-light-emitting particle has entered into the light detection region when a signal whose light intensity is lower than a predetermined threshold value measured from the intensity of the background light is detected. Concretely, in the step of detecting the signal indicating the existence of the single particle individually, a upwardly convex, bell-shaped pulse form signal whose intensity is higher than a predetermined threshold value measured from the intensity of the background light in the time series light intensity data may be detected as the signal indicating the existence of the light-emitting particle, and a downwardly convex, bell-shaped pulse form signal whose intensity is lower than a predetermined threshold value measured from the intensity of the background light in the time series light intensity data may be detected as the signal indicating the existence of the single particle, and in this case, the time series light intensity data may be smoothed and a bell-shaped pulse form signal in the smoothed time series light intensity data may be detected as a signal indicating the existence of a single particle. Alternatively, in another manner of individual detection of signals indicating the respective existences of different single particles, the detection of a signal of a single particle may conducted by computing the probabilities for a pattern of the time variation of light intensity value appearing on time series light intensity data in the respective cases of the presence and absence of a single particle in the light detection region, and judging whether the pattern of the time variation of the light intensity value is prone to be generated in a case that a single particle exists in the light detection region or in a case that no single particles exist.

Furthermore, the moving speed of the position of the light detection region in the sample solution may be appropriately changed based on the characteristics, number density or concentration of the single particle in the sample solution, and preferably, the moving speed of the position of the light detection region in the sample solution is set higher than the diffusion moving velocity of the single particle to be an object to be detected. The moving of the position of the light detection region in the sample solution may be done by an arbitrary way, and preferably, the position of the light detection region may be changed by changing the optical path of the optical system of the microscope or by moving the position of the sample solution. The movement track of the position of the light detection region may be set arbitrarily, for example, which is selectable from circular, elliptical, rectangular, straight and curvilinear ones.

Further, the above-mentioned method may also comprise a step of counting a number of the signals indicating the existences of the single particles individually detected during moving the position of the light detection region to count a number of the single particles and/or a step of determining a number density or concentration of the single particle in the sample solution based on the number of the detected single particles. In this regard, also in the case of the above-mentioned method, typically, the counting of particles is conducted by counting the number of signals of single particles obtained in a arbitrarily set measuring time; however, the measurement may be performed until the number of signals of single particles reaches an arbitrarily set number, and the single particle concentration value may be computed based on the measuring time. Thus, the above-mentioned method may be designed to repeat the moving of the position of the light detection region of the optical system by the light detection region mover, the detecting of the light from the light detection region and the detecting of the signals indicating the existences of the single particle by the signal processor until the number of the signals indicating the existences of the single particles detected with the signal processor reaches a predetermined number; and to determine a concentration of the single particle in the sample solution based on the time taken for the number of the signals indicating the existences of the single particles to reach the predetermined number.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a liposome, metallic colloid, a bead (a magnetic bead, a polystyrene bead, a latex bead, etc.), a quencher (azobenzenes (dabcyl, BHQ, etc.), a metallic particle etc.), and it should be understood that such a case belongs to the scope of the present invention also.

Effect of Invention

Briefly, the single particle detection technique of the present invention is a technique which conducts the detection of single particles when a light-emitting particle and a non-light-emitting particle are dispersed in a solution in accordance with the scanning molecule counting method. It should be understood that, according to the inventive technique, it becomes possible to detect the existences of a light-emitting particle and a non-light-emitting particle simultaneously by the light measurement in one detected light wavelength band. Accordingly, in the inventive technique, by preparing a light-emitting particle and a non-light-emitting particle as different kinds of particle to be observed, the detection of their existences, the counting of particles, the concentration detection, etc. for each kind become possible in one-time measurement for the particles to be observed of two kinds.

Other purposes and advantages of the present inventions will become clear by explanations of the following preferable embodiments of the present invention.

BRIEF DESCRIPTIONS OF DRAWINGS

FIG. 1A is a schematic diagram of the internal structure of a single particle detection device performing the scanning molecule counting method in accordance with the present invention. FIG. 1B is a schematic diagram of a confocal volume (a light detection region of a confocal microscope). FIG. 1C is a schematic diagram of the mechanism for changing the direction of the mirror 7 to move the position of a light detection region in a sample solution. FIG. 1D is a schematic diagram of the mechanism for moving the horizontal position of a micro plate to move the position of the light detection region in a sample solution.

FIGS. 2A and 2B are a schematic diagram explaining the principle of detecting the existence of a single particle and a schematic diagram of the variation of the measured light intensity with time in the scanning molecule counting method of the present invention, respectively.

FIG. 3 is a diagram showing one manner of procedures (the smoothing of time series light intensity data and the detection of a single particle signal by fitting a bell shaped function) of the scanning molecule counting method performed in accordance with the present invention in the form of a flow chart.

FIGS. 4A and 4B are drawings of models in a case that a single particle crosses a light detection region owing to the Brownian motion and in a case that a single particle crosses a light detection region by moving the position of the light detection region in a sample solution at a velocity quicker than the diffusional moving velocity of the single particle. FIG. 4C shows drawings explaining an example of the signal processing step of the detected signals in the procedure for detecting the existence of a single particle from the measured time series light intensity data (change in time of photon count) in accordance with the processes of FIG. 3.

Figure 5A:
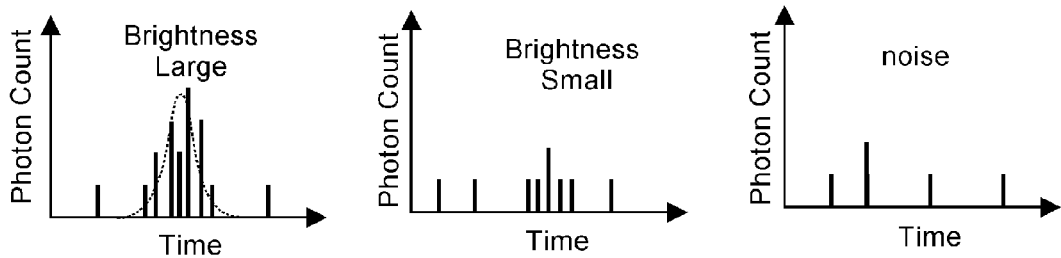
Figure 5B:
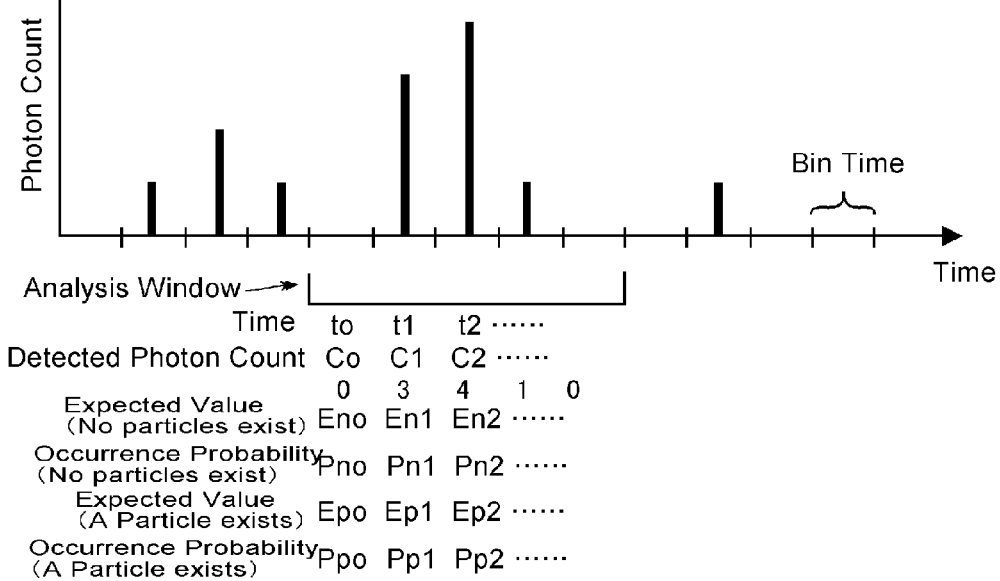
Figure 5C:
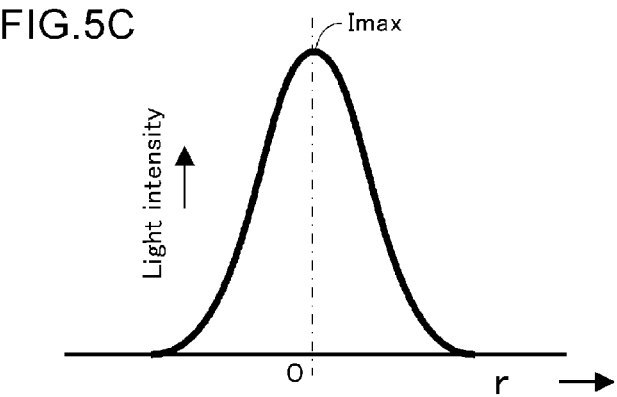

FIG. 5A is a drawing explaining about the principle of the detection of a single particle signal based on the occurrence probabilities of light intensity variation in time series light intensity data. 5A shows typical examples of time series light intensity data. (Left) A case that a light-emitting particle with large brightness exists. (Middle) A case that a light-emitting particle with small brightness exists. (Right) A case that no light-emitting particles exist. FIG. 5B is a drawing explaining the analysis window set on time series light intensity data in the present invention. FIG. 5C shows the light intensity distribution in a light detection region.

FIG. 6 is a diagram showing another manner of procedures (the detection of a single particle signal based on the occurrence probabilities of light intensity variation in time series light intensity data) of the scanning molecule counting method performed in accordance with the present invention in the form of a flow chart.

FIG. 7 is a diagram showing an alternative manner of procedures (a case that the detection of a single particle signal is performed until the particle count reaches to a predetermined particle count) of the scanning molecule counting method performed in accordance with the present invention in the form of a flow chart.

Figure 8A:
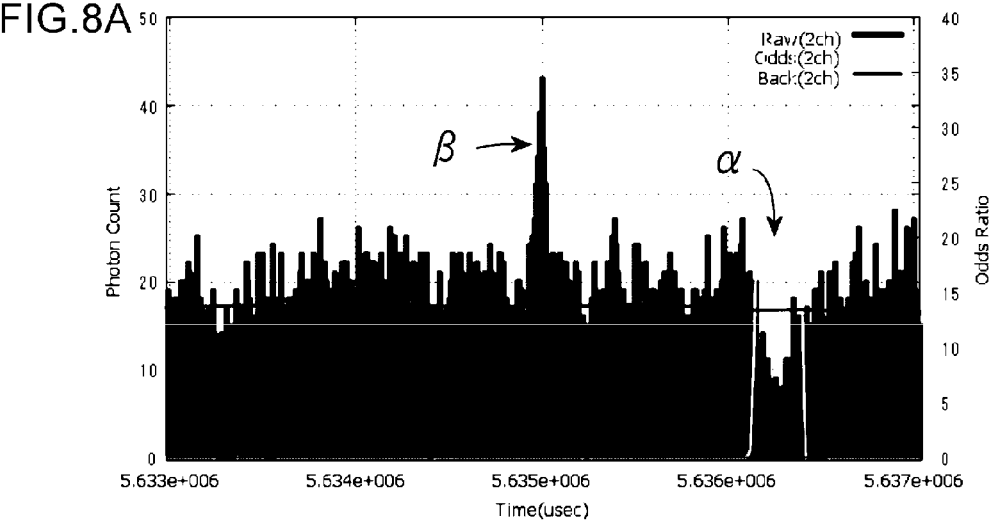
Figure 8B:
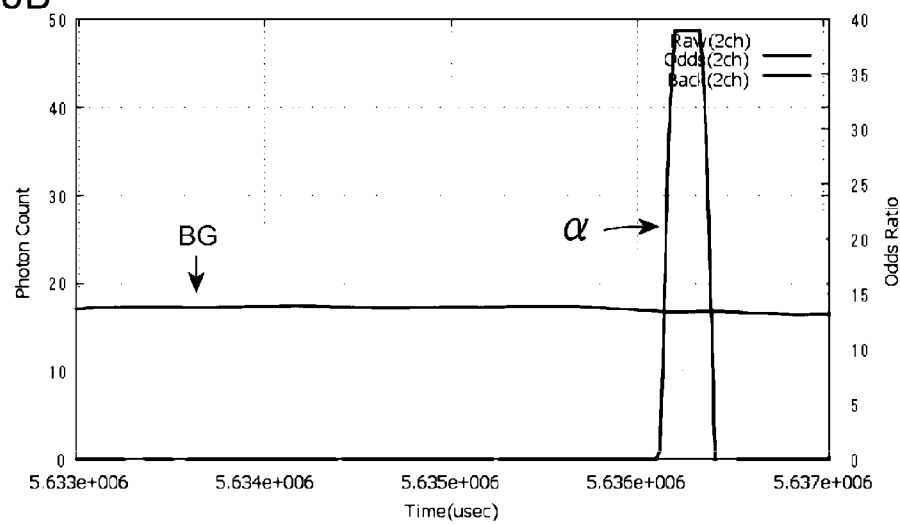
Figure 8C:
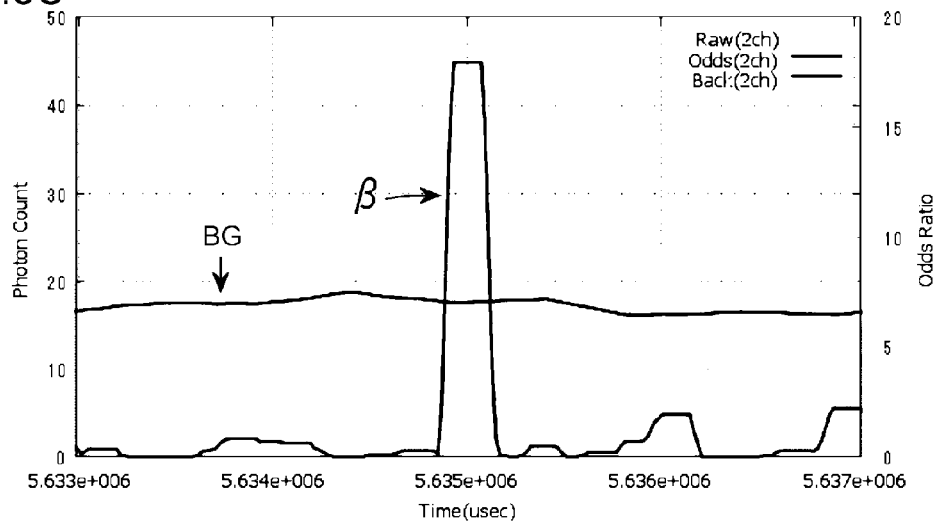

FIG. 8A shows a part of time series light intensity data (photon count data) obtained in accordance with the scanning molecule counting method in accordance with the present invention. FIG. 8B shows odds ratios of the occurrence probabilities computed in assuming a case that a non-light-emitting particle exists and a case that no non-light-emitting particles exist, respectively, in the data of 8A; and FIG. 8C shows odds ratios of the occurrence probabilities computed in assuming a case that a light-emitting particle exists and a case that no light-emitting particles exist, respectively, in the data of 8A.

Figure 9:
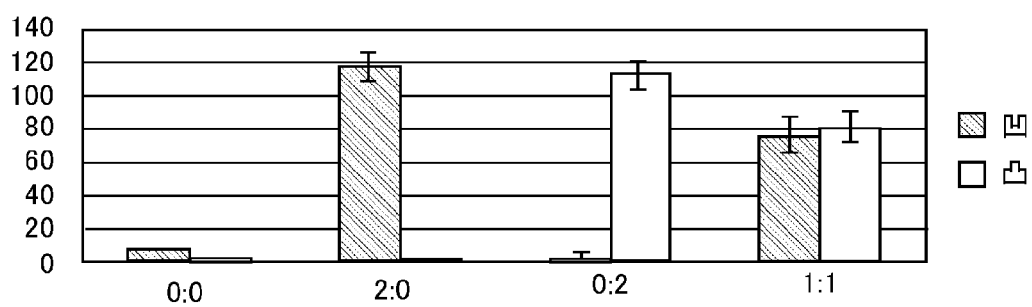

FIG. 9 shows average values (bar graph) and standard deviations (error bar) of the numbers of pulses, detected in accordance with the scanning molecule counting method in accordance with the present invention, for a solution containing no particles (0:0), a solution containing only a non-light-emitting particle (2:0), a solution containing only a light-emitting particle (0:2) and a solution containing a light-emitting particle and a non-light-emitting particle (1:1).

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14a - - - Dichroic mirror or polarization beam splitter
14 - - - Barrier filter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

Structure of Single Particle Detection Device

Figures 1A, 1B, 1C, 1D:
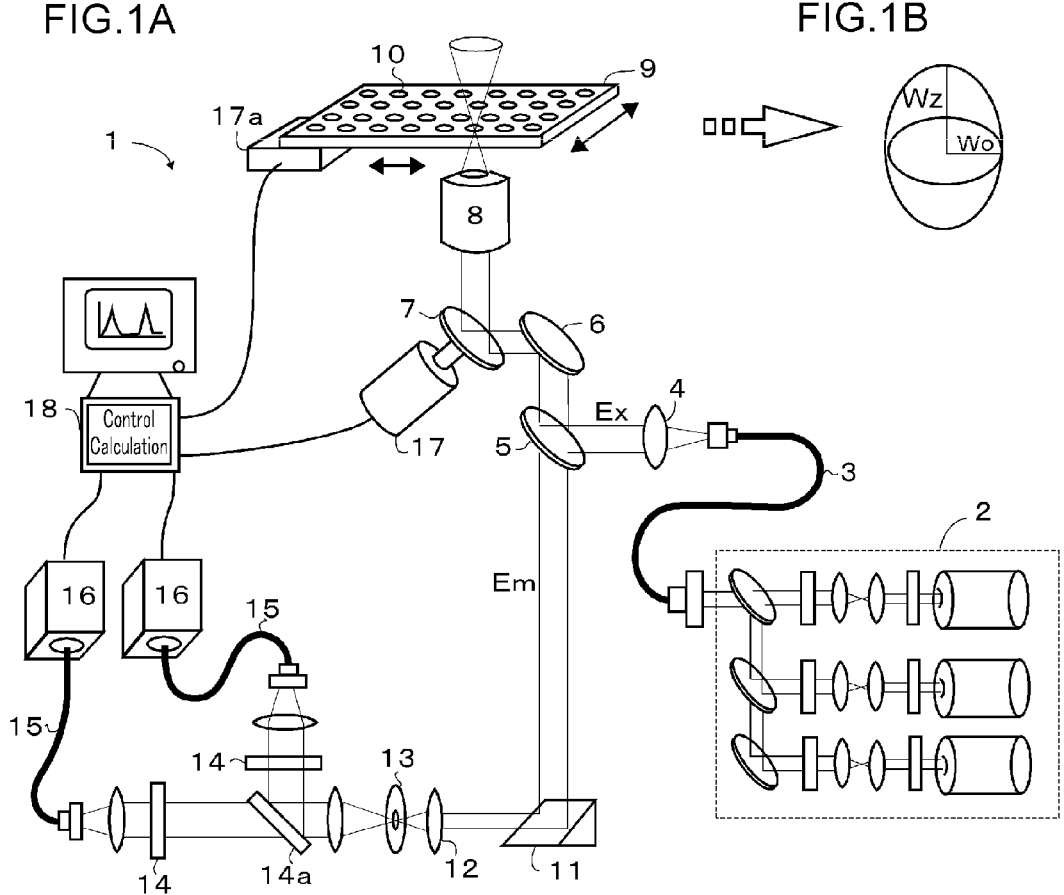

In the basic structure, a single particle detection device which realizes the single particle detection technique according to the present invention can be a device constructed by associating the optical system of a confocal microscope and a photodetector, enabling FCS, FIDA, etc., as schematically illustrated in FIG. 1A. Referring to this drawing, the single particle detection device 1 consists of an optical system 2-17 and a computer 18 for acquiring and analyzing data together with controlling the operation of each part in the optical system. The optical system of the single particle detection device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8.

Above the objective 8, typically, there is placed a sample container or a micro plate 9 having wells 10 arranged thereon, to which one to several tens of µL of a sample solution is dispensed, and the laser light emitted from the objective 8 is focused in the sample solution in the sample container or well 10, forming a region having strong light intensity (excitation region). In this regard, in the sample solution, typically, light-emitting particles and non-light-emitting particles to be objects to be observed and arbitrary light-emitting substance which produces background light are dispersed or dissolved, and when no particles to be observed have entered into the excitation region, the light-emitting substance is excited so that substantially constant light is emitted, becoming the background light; and when a non-light-emitting particle enters into the excitation region, the background light will decrease, while, when a light-emitting particle enters into the excitation region, the light intensity will increase.

Then, the light (Em), emitted from the excitation region, passes through the objective 8 and the dichroic mirror 5, and the light is reflected on the mirror 11 and condensed by a condenser lens 12, and then the light passes through the pinhole 13 and transmits through the corresponding barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for the single particle detection are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with a Gaussian distribution having the peak at the center of the region. The effective volume is a volume of an approximate ellipsoid bordering a surface where the light intensity is reduced to $1/e^2$ of the peak intensity.), which is called as "confocal volume".

Further, in the present invention, there is detected a light amount increase or reduction because of the existence of a single particle in the presence of the background light which consists of faint light from several number of fluorescent dye molecules, and thus, for the photodetector 16, preferably, a super high sensitive photodetector, usable for the photon counting, is used. When the detection of light is performed by the photon counting, the measurement of light intensity is performed for a predetermined time in a manner of measuring the number of photons which have sequentially arrived at a photodetector in every predetermined unit time (BIN TIME). Thus, in this case, the time series light intensity data is time series photon count data. Also, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, in the presences of two or more specimens, quick measurements are achievable.

Furthermore, in the optical system of the above-mentioned single particle detection device, there is further provided a mechanism for scanning the inside of the sample solution with the light detection region, namely for moving the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the way of moving the absolute position of the light detection region). This mirror deflector 17 may be the same as that of a galvanomirror device equipped on a usual laser scan type microscope. Alternatively, as illustrated in FIG. 1D, the stage position changing apparatus 17a may be operated to move the horizontal position of the container 10 (micro plate 9) in which the sample solution is dispensed, thereby moving the relative position of the light detection region in a sample solution (the way of moving the absolute position of a sample solution.). Even in either of cases, in order to attain a desired moving pattern of the position of the light detection region, the mirror deflector 17 or stage position changing apparatus 17a is driven in harmony with the light detection of the photodetector 16 under the control of the computer 18. The movement track of the position of the light detection region may be arbitrarily selected from circular, elliptical, rectangular, straight and curvilinear ones, or a combination of these (The program in the computer 18 may be designed so that various moving patterns can be selected.). Moreover, by combining the way of moving the absolute position of the light detection region and the way of moving the absolute position of the sample solution, the absolute position of the light detection region may be moved together with moving the position of the sample solution. In this case, it is avoided that the same single particle is repetitively detected because of the light detection region passing through the same region in a short time. Or, by making the light detection region repetitively pass through the same region intentionally through the way of moving the absolute position of the light detection region so as to periodically detect the same single particle multiple times, the improvement in the accuracy of signals may be achieved. In this case, after performing the moving of the absolute position of the light detection region for a predetermined time, by moving the position of the sample solution intermittently and repeating the similar detection of a single particle in a different place in the sample solution, the increase of the number of the single particles may be achieved. In this regard, although not illustrated, the position of the light detection region may be moved in the vertical direction by moving the objective 8 up and down, so that the track of the position of the light detection region is developed in three dimensions within the sample solution.

In the case that the light-emitting particle to be a particle to be observed and the light-emitting substance which generates background light emit light by multiple photon absorption, the above-mentioned optical system is used as a multiphoton microscope. In that case, since the light is emitted only from the focal region of the excitation light (light detection region), the pinhole 13 may be removed. When substance which generates background light emits light owing to a chemiluminescence or bioluminescence phenomenon without excitation light, the optical system 2-5 for generating excitation light may be omitted. When substance which generates background light emits light owing to phosphorescence or scattered light, the above-mentioned optical system of the confocal microscope is used as it is. Moreover, background light may be provided by illumination light. In that case, the sample solution is illuminated with transmitted illumination (which may be Koehler illumination.) from above the objective.

Furthermore, in the optical analysis device 1, as shown in the drawing, two or more excitation light sources 2 may be provided so that the wavelength of the excitation light can be appropriately selected in accordance with the wavelength of the light for exciting the light-emitting particle or light-emitting substance. Moreover, two or more photodetectors 16 may also be provided such that the respective photodetectors 16 may be designed to separately detect mutually different components in the light from the light detection region. In that case, in the detected light optical path after the passage through the pinhole 13, a mechanism for dividing the optical path in an arbitrary manner is provided. For example, by inserting a dichroic mirror 14a which reflects the light of a particular wavelength band and allows the other wavelength band to penetrate therethrough into the site 14a in the detected light optical path, the light components of mutually different wavelength bands become separately detectable.

The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disk, a magnetic optical disk, a CD-ROM, a DVD-ROM, a semiconductor memory, etc. Furthermore, the above-mentioned program may be distributed to a computer through communication line, and the computer which has received this distribution may be made to execute the program.

The Principle of Single Particle Detection of the Present Invention

As described in the column of "Summary of Invention", in the single particle detection technique of the present invention, briefly, in a case that a light-emitting particle and a non-light-emitting particle are included in a sample solution, time series light intensity data are obtained by measuring the light of a light detection region under the existence of background light in accordance with the scanning molecule counting method, and then, in the time series light intensity data, a significant increase of light intensity is detected as a signal of a light-emitting particle while a significant reduction of light intensity is detected as a signal of a non-light-emitting particle. According to this structure, in one time light measurement for one detected light wavelength band, it becomes possible to conduct the detection of particles of two mutually different kinds as particles to be observed, the counting of those particles, or the acquisition of the information about concentrations of those particles in the sample solution, etc. In the followings, the principle of the scanning molecule counting method according to the present invention is explained.

In "the scanning molecule counting method" (patent documents 9-11), basically, the light detection is performed together with moving the position of the light detection region CV in a sample solution, namely, scanning the inside of the sample solution with the light detection region CV by driving the mechanism (mirror deflector 17) for moving the position of the light detection region to change the optical path or by moving the horizontal position of the container 10 (micro plate 9) into which the sample solution is dispensed, as schematically drawn in FIG. 2A. In that time, especially in the case of the present invention, background light is made emitted from the light detection region (or the light detection region is illuminated with illumination light), and thereby the background light is detected almost uniformly during the moving of the light detection region CV (time to-t3 in the drawing). Then, when the light detection region CV passes through a region where one light-emitting particle exists (t1), the light is emitted from the light-emitting particle in addition to the background light, and therefore, there appears a significant, bell-shaped pulse form increase of light intensity on the time series light intensity data as drawn in FIG. 2B. Also, when the light detection region CV passes through a region where one non-light-emitting particle exists (t2), the light amount from the light detection region CV will decrease, and therefore, as drawn in FIG. 2B, there appears a significant, bell-shaped pulse form reduction of light intensity on the time series light intensity data. Thus, by conducting the moving of the position of the light detection region CV and the light detection as described above, and detecting pulse form signals (significant light intensity increase and reduction) appearing during that period as illustrated in FIG. 2B one by one, a light-emitting particle and a non-light-emitting particle are individually detected while being discriminated from one another also, and by counting each number of the light-emitting particles and the non-light-emitting particles, it becomes possible to acquire the information about the number, concentration or number density of the light-emitting particle and the information about the number, concentration, or the number density of the non-light-emitting particle, existing in the measured region.

As noted above, in order to achieve the detection of a signal of a light-emitting particle and a signal of a non-light-emitting particle in the presence of background light, it is required that the relation between the emitted light intensity of a light-emitting particle and background light intensity and the relation between the emitted light intensity of a non-light-emitting particle and background light intensity have been adjusted appropriately. With respect to the relation between the emitted light intensity of the light-emitting particle and background light intensity, briefly, the light intensity in the detected light wavelength band of the whole light detection region at a time when a light-emitting particle exists in the light detection region, namely, when a light-emitting particle occupies a portion of the space in the light detection region should be higher than the light intensity in the detected light wavelength band of the whole light detection region at the time when no light-emitting particles exist in the light detection region, and thus, in the detected light wavelength band, the emitted light amount of the light-emitting particle per unit volume is made larger than the light amount of the background light per unit volume. However, actually, background light intensity is not completely constant, and thus, the emitted light intensity of a light-emitting particle and/or background light intensity are adjusted so that the emitted light amount of a light-emitting particle per unit volume will be sufficiently larger than the light amount of the background light per unit volume (Concretely, both light intensities may be adjusted experimentally.)

On the other hand, with respect to the relation between the emitted light intensity of a non-light-emitting particle and background light intensity, the light intensity in the detected light wavelength band of the whole light detection region at a time when a non-light-emitting particle exists in a light detection region, namely, when a non-light-emitting particle occupies a portion of the space in the light detection region should be lower than the light intensity in the detected light wavelength band of the whole light detection region at a time when no non-light-emitting particles exist in the light detection region. Thus, for the non-light-emitting particle, the emitted light intensity of a non-light-emitting particle and the background light intensity are adjusted so that the emitted light amount of the non-light-emitting particle per unit volume in the detected light wavelength band will be smaller than the light amount of the background light per unit volume (That is, it should be understood that, since the emitted light intensity of a non-light-emitting particle in a detected light wavelength band should just be lower than background light, the non-light-emitting particle may not be a particle which emits no light absolutely.).

In this regard, for the non-light-emitting particle, the degree of reduction of light intensity can be estimated from the relation between the diameter of a non-light-emitting particle and the diameter of a light detection region. Typically, the light intensity distribution in the light detection region has the maximum intensity Imax at its center and a bell-shaped profile f(r) reducing in the direction of radius r (see FIG. 5C). Thus, using the radius a of the light detection region at which f(r) becomes almost 0, the total amount $\alpha$ of the light emitted from the inside of the light detection region when no non-light-emitting particles exist in the light detection region is given by:

$$\alpha = 4\pi \int r^2 f(r) dr \text{ [integration interval is 0-}a\text{]}$$

On the other hand, when a non-light-emitting particle of radius b enters into the light detection region and exists at the center of the light detection region, the space which gives the background light (in the following, referred to as "light-emitting space") in the center region will be eliminated, so that the light amount equivalent to the eliminated light-emitting space will decrease. The light amount equivalent to this eliminated light-emitting space, i.e., the decrease amount $\beta$ is given by:

$\beta=4\pi\int r^2 f(r)dr$ [integration interval is $0-b$].

Then, the ratio of the light intensity reduction can be estimated by $\beta/\alpha$. Here, when f (r) is a Gauss function while $\alpha=1$ and $a=1$ are supposed, $f(r)=0.684\exp(-2r^2)$ is obtained. Typically, the variation ratio of background light is about 1%, and so, if the reduction percentage of the light intensity owing to a non-light-emitting particle is 1% or less, the detection of a signal would become impossible, and thus, according to the calculation with the above-mentioned expression, the ratio of the radius of a non-light-emitting particle to the radius of a light detection region, b/a, should be made 0.15 or more. Moreover, when the reduction ratio of the light intensity owing to a non-light-emitting particle is made to be not less than 10%, the ratio of the radius of a detectable non-light-emitting particle to the radius of a light detection region, b/a, becomes 0.35. In this regard, when the non-light-emitting particle to be observed is an acceptor or a quencher of a fluorescence energy transfer, such a non-light-emitting particle absorbs light in its circumference (for example, 10 nm), and thus, a detectable non-light-emitting particle radius can be reduced in comparison with the radius as illustrated above. Further, when a non-light-emitting particle emits light, a detectable non-light-emitting particle radius may increase rather than the radius as illustrated above.

Thus, in the inventive single particle detection technique as described above, no statistical operation processing, such as fluorescence intensity fluctuation calculation, is performed, and particles are detected on by one, and therefore, the acquisition of the information on a concentration or number density of a particle is possible even in a sample solution of a low concentration of particle to be observed, at which an sufficiently accurate analysis is not possible by conventional FCS and FIDA, etc. Further, especially according to the presence of significant background light, the influence of stray light or Raman scattering light is advantageously reduced. Further, it is important to note that, in the inventive single particle detection technique, it is possible to discriminate between the signal of a light-emitting particle and the signal of a non-light-emitting particle in the light intensity data of one detected light wavelength band (1 ch of light intensity data), and therefore, the detection of particles of two mutually different kinds can be achieved simultaneously in a manner that identifies their kinds. This feature is very advantageous in an analysis of molecular interaction, etc.

Operation Processes of Scanning Molecule Counting Method

In the embodiment of the scanning molecule counting method in accordance with the present invention with the single particle detection device 1 as illustrated in FIG. 1A, concretely, there are conducted (1) the preparation of a sample solution containing single particles and light-emitting substance generating background light; (2) the process of measuring the light intensity of the sample solution and (3) the process of analyzing measured light intensities. FIG. 3 shows the processes in this embodiment in form of the flow chart.

(1) Preparation of a Sample Solution

The particle to be an observed object in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological molecules. For a light-emitting particle, when a particle to be observed is not a particle which emits light inherently, there is used one obtained by adding a light emitting label (a fluorescence molecule, a phosphorescence molecule, chemi- or a bioluminescent molecule) to a particle to be an observed object in an arbitrary manner. As for a non-light-emitting particle, it may be an arbitrary particle similarly to the light-emitting particle. Further, background light may be fluorescence, autofluorescence, light of scattering (Raman scattering (solvent (water), carbon disulfide, isoprene, transition metal complex) or light-emitting substance, or alternatively, it may be illumination light with a uniform light source. When the background light is given by dispersion of light-emitting substance, the light-emitting substance may be arbitrary light-emitting molecules, such as fluorescent molecules, phosphorescent molecule, chemi- and a bioluminescent molecule, and those are dissolved or dispersed in a sample solution at a concentration where more than several molecules always exist in the light detection region. In this regard, as noted above, the light amount of the background light is appropriately adjusted so as to be smaller than the light amount of the light-emitting particle to be observed and larger than the light amount of the non-light-emitting particle to be observed per unit volume. The sample solution is typically an aqueous solution, but not limited to this, and it may be an organic solvent or other arbitrary liquids.

(2) Measurement of Light Intensity of Sample Solution (FIG. 3—step 100)

The light intensity measurement in the optical analysis by the scanning molecule counting method of the present embodiment may be performed in a manner similar to the measuring process of light intensity in FCS or FIDA except that the moving of the position of the light detection region in a sample solution (scanning in a sample solution) is conducted by driving the mirror deflector 17 or stage position changing apparatus 17a during the measurement. In the operation processes, typically, after dispensing a sample solution into the well(s) 10 of the micro plate 9 and putting it on the stage of the microscope, when a user inputs to the computer 18 a command of starting a measurement, the computer 18 executes programs memorized in a storage device (not shown) (the process of moving the position of the light detection region in the sample solution, and the process of detecting light from the light detection region during the moving of the position of the light detection region) to start radiating the excitation light and measuring the light intensity in the light detection region. During this measurement, under the control of the operation process of the computer 18 according to the programs, the mirror deflector 17 or the stage position changing apparatus 17a, drives the mirror 7 (galvanomirror) or the micro plate 9 on the stage of the microscope to move the position of the light detection region in the well 10, and simultaneously with this, the photodetector 16 sequentially converts the detected light into electric signals and transmits it to the computer 18, which generates the time series light intensity data from the transmitted signals and stores it in an arbitrary manner. The photodetector 16 is typically a super high sensitive photodetector which can detect the presence or absence of an arrival of a single photon, and thus, when the light detection is conducted by the photon counting, the time series light intensity data will be a time series photon count data.

The moving speed of the position of the light detection region during the measurement of the light intensity may be a predetermined velocity set arbitrarily, for example, experimentally or in order to meet the purpose of an analysis. In a case of acquiring the information on the number density or concentration based on the number of detected single particles, the region size or volume through which the light detection region has passed is required, and therefore, the moving of the position of the light detection region is performed in a manner enabling the grasping of the moving distance. In this regard, because the interpretation of a measurement result will become easy if the elapsed time is proportional to the moving distance of the position of the light detection region, basically, it is preferable that the moving speed is constant, although not limited thereto.

By the way, regarding the moving speed of the position of the light detection region, in order to perform quantitatively precisely individual detection of a single particle to be observed from the measured time series light intensity data or the counting of the number of single particles, it is preferable that the moving speed is set to a value quicker than the moving speed in the random motion, i.e., the Brownian motion of a single particle. Since the particle to be observed in the inventive single particle detection technique is a particle dispersed or dissolved in a solution and moving at random freely, its position moves with time owing to the Brownian motion. Thus, when the moving speed of the position of the light detection region is slower than the movement of a particle owing to the Brownian motion, the particle moves at random in the region as schematically drawn in FIG. 4A, whereby the light intensity varies at random (as noted, the excitation light intensity in the light detection region is reduced from the peak at the center of the region toward its outside.), so that it becomes difficult to determine a significant light intensity variation corresponding to each single particle. Then, preferably, as drawn in FIG. 4B, the moving speed of the position of the light detection region is set to be quicker than the average moving speed of a particle by the Brownian motion (diffusional moving velocity) so that the particle will cross the light detection region in an approximately straight line and thereby the profile of the change of the light intensity corresponding to each particle becomes almost uniform in the time series light intensity data as illustrated in the most upper row of FIG. 4C (When a single particle passes through the light detection region in an approximately straight line, the profile of the light intensity change is similar to the inverted form of the excitation light intensity distribution.) and the correspondence between each particle and light intensity can be easily determined.

Concretely, the time $\Delta t$ required for a particle having a diffusion coefficient D to pass through the light detection region of radius Wo (confocal volume) by the Brownian motion is given from the Expression of the relation of mean-square displacement:

$$(2Wo)^2 = 6D \cdot \Delta t$$

as:

$$\Delta t = (2Wo)^2 / 6D,$$

and thus, the velocity of the particle moving by the Brownian motion (diffusional moving velocity) Vdif, becomes approximately $$Vdif = 2Wo/\Delta t = 3D/Wo$$

Then, with reference to this, the moving speed of the position of the light detection region may be set to a value sufficiently quicker than Vdif. For example, when the diffusion coefficient of a particle to be observed is expected to be about $D=2.0\times10^{-10}$ m$^2$/s, Vdif will be $1.0\times10^{-3}$ m/s, supposing Wo is about 0.62 μm, and therefore, the moving speed of the position of the light detection region may be set to its 10 times or more, such as 15 mm/s. In this regard, when the diffusion coefficient of a particle to be observed is unknown, an appropriate moving speed of the position of the light detection region may be determined by repeating the executions of a preliminary experiment with setting various moving speeds of the position of the light detection region in order to find the condition that the profile of a light intensity variation becomes an expected profile (typically, similar to the excitation light intensity distribution).

(3) Analysis of Light Intensity

When the time series light intensity data in the sample solution is obtained by the above-mentioned processes, there are performed detection of a signal of a single particle, counting of single particles, and various analyses, such as concentration calculation, etc. in the computer 18 through processes in accordance with programs memorized in a storage device.

(i) Individual Detection of a Signal of a Single Particle Through Smoothing and Bell-Shaped Function Fitting of Time Series Light Intensity Data When the track of one particle in its passing through the light detection region is approximately straight as shown in FIG. 4B, the light intensity variation in the signal corresponding to the particle in the time series light intensity data has an almost bell shaped profile reflecting the light intensity distribution in the light detection region (determined by the optical system). Referring to the most upper row of FIG. 4C, especially when a non-light-emitting particle (α) passes through the light detection region, the light intensity variation becomes downwardly convex, and when a light-emitting particle (β) passes through the light detection region, the light intensity variation becomes upwardly convex. Thus, in one manner of the individual detection of a single particle signal, basically, when the time width for which a reduction of the light intensity descending below an appropriately set threshold value measured from the background light continues is in a predetermined range, and when the time width for which an increase of the light intensity ascending above an appropriately set threshold value measured from the background light continues is in a predetermined range, each signal having the profile of the light intensity reduction or increase may be judged to correspond to one particle having passed through the light detection region, and thereby the detection of one particle will be achieved. Further, when the light intensity distribution in the light detection region can be assumed as a Gaussian distribution, downwardly convex or upwardly convex from the background light Ibg:

$$I = Ibg - A^- \cdot \exp(-2t^2/a^2) \qquad (\alpha),$$

$$I = Ibg + A^+ \cdot \exp(-2t^2/a^2) \qquad (\beta),$$

and when the intensity $A^-$, $A^+$ and the width a, computed by fitting Expression (α) or Expression (β) to the profile of a significant light intensity reduction or increase (a profile which can be clearly judged not to be a fluctuation of the background light), are within the respective predetermined ranges, the profile of the light intensity may be judged to correspond to one particle having passed through the light detection region, and thereby the detection of one particle will be done (The signal with the intensity $A^-$, $A^+$ and the width a out of the predetermined ranges may be judged as a noise or a contaminant signal and ignored in the later analysis, etc.).

As an example of processing methods of performing collective detections of single particles from time series light intensity data, first, a smoothing treatment is performed to the time series light intensity data (FIG. 4C), the most upper row "detected result (unprocessed)") (FIG. 3A—step 110, FIG. 4C mid-upper row "smoothing"). The light emissions by a light-emitting particle to be an observed particle and the substance, etc. giving the background light are stochastic and the light intensity is comparatively weak so that minute increases and decreases of the light intensity will occur, and such minute increases and decreases (fluctuation) in the light intensity would deteriorate the detection accuracy of a signal indicating the existence of a single particle. The smoothing makes it possible to disregard such minute increases and decreases on the data. The smoothing treatment may be done, for example, by the moving average method (e.g. adjacent average method, Savinsky-golay algorithm), Percentile filter method, FFT filter method. In this regard, parameters in performing the smoothing treatment, e.g., the number of datum points in one time of the averaging, the number of times of the moving average, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differential values with time of the time series light intensity data after the smoothing treatment are computed (step 120). As illustrated in FIG. 4C, the mid-low row "time differential", in the time differential values of time series light signal data, the variation of the value increases at the time of the signal value change, and thereby, the start point and the end point of a significant signal can be determined advantageously by referring to the time differential values.

After that, a significant pulse signal is detected sequentially on the time series light intensity data, and it is judged whether or not the detected signal is a signal corresponding to a single particle. Concretely, first, on the time series time-differential value data of the time series light intensity data, the start point and the end point of one pulse signal are searched and determined by referring to the time differential values sequentially, so that a pulse existing region will be specified (step 130). When one pulse existing region has been specified, to the smoothed time series light intensity data in the pulse existing region, the fitting of a upwardly convex, bell-shaped function is applied in a region of an upwardly convex light intensity variation and the fitting of a downwardly convex, bell-shaped function is applied in a region of an downwardly convex light intensity variation (FIG. 4C, the lower row "bell-shaped function fitting"), and then, parameters of the pulse of the bell-shaped function, such as the peak intensity (Maximum reduction amount from the background light), Ipeak; the pulse width (full width at half maximum), Wpeak; the correlation coefficient in the fitting (of the least square method), etc. are computed (step 140). In this regard, although the bell-shaped function to be used in the fitting is typically a Gauss function, it may be a Lorentz type function. Further, the direction of a light intensity variation in a pulse existing region is identified with the order of the increase and decrease in the start point and the end point of the time differential values. Then, it is judged whether or not the computed parameters of the bell shaped function are within the ranges assumed for the parameters of the bell-shaped profile drawn by a pulse signal detected when one single particle passes the light detection region, namely, whether or not the peak intensity ($A^-$ of Expression $\alpha$ or $A^+$ of Expression $\beta$, the maximum value of the reduction amount of the background light or the increase amount), pulse width and the correlation coefficient of the pulse are in the predetermined ranges, respectively, for instance, whether or not the following conditions:

20 μsec.<pulse width<400 μsec.

Peak intensity>4.0[$pc$/10 μsec.]

Correlation coefficient>0.95  (A)

are satisfied, etc. (step 150) Then, a signal whose computed parameters of the bell shaped function are within the ranges assumed for a signal corresponding to one signal is judged as a signal corresponding to one particle. On the other hand, a pulse signal whose computed parameters of the bell type function are not within the assumed ranges is disregarded as noise.

The searching and judgment of a pulse signal in the above-mentioned processes of steps 130-150 may be repetitively performed over the whole region of time series light intensity data (Step 160). In this embodiment, especially, in the searching and judging of pulse signals, whether a signal is upwardly convex or downwardly convex is identified one by one, and the numbers of the respective pulse signals may be counted separately.

(ii) Individual Detection of a Signal of a Single Particle Based Upon Occurrence Probabilities of Light Intensity Variations in Time Series Light Intensity Data For an alternative manner of the individual detection of a single particle signal, the existence of a signal of a single particle may be detected based upon the occurrence probabilities computed for the pattern of the light intensity variation (photon count variation) appearing in time series light intensity data (see Japanese patent application No. 2012-32421). Referring to FIG. 5A, generally, in a case where time series light intensity data is photon count data, the light intensity value is a detected photon count per bin time. Thus, as illustrated in the drawing, the light intensity value is discretely distributed in the time base direction. In that case, a particle signal with large brightness is less influenced with noise signals and has an approximately bell shaped profile (Left figure); however, as for a particle signal with small brightness, its intensity value becomes almost similar to that of a noise signal and a noise signal is further superposed thereon (Middle figure), and thus, it becomes difficult to extract the approximately bell shaped profile, and so, its discrimination from a time region in which only a noise signal exists without particles (right figure) becomes difficult. However, between the time region in which a particle signal with small brightness exists and the time region in which only noise signals exist, there are differences in the occurrence frequency and the patterns of phenomena of a photon being detected (phenomena that the photon count becomes one or more). The similar phenomenon can be observed also between the signal of a non-light-emitting particle and the fluctuation of the background light. Then, for a time variation of light intensity value (photon count sequence) in each predetermined time width on time series light intensity data, a probability that the time variation of light intensity value would occur in assuming that a particle exists in the light detection region (occurrence probability (in the presence of a particle)) and a probability that the time variation of light intensity value would occur in assuming that no particles exist in the light detection region (occurrence probability (in the absence of particles)) are computed, and then, the condition giving the higher occurrence probability is estimated to be the actual condition.

More concretely, first, referring to FIG. 5B, in time series light intensity data, there are set sections of an arbitrary time width (hereafter, called as an analysis window). The analysis window has a photon count Ci detected in each unit time (usually, it may be a bin time.), ti, (i=1, 2, . . . the same in the following.). By the way, it is thought that the number of events of photon detections occurring in each unit time follows the Poisson distribution having the expected value in the corresponding unit time, and therefore, in an arbitrary unit time ti, a probability that the detected photon count Ci occurs (unit time occurrence probability) is given by:

[Exp. 1]

$$Pi = \frac{Ei^{Ci}}{Ci!} \exp(-Ei) \quad (1)$$

Here, Ei is the expected value of the photon count in the unit time ti. And when n+1 unit times are included in an analysis window, the probability P that the detected photon count sequence Ci occurs in the analysis window (occurrence probability) is given by:

[Exp. 2]

$$P = \prod_{i=0}^{n} Pi \quad (2)$$

The above-mentioned expected value Ei of the number of the occurrences of the photon detection events in each unit time ti is determined depending upon the presence or absence of a particle in the light detection region in a time region corresponding to an analysis window under the light measurement. Thus, when no particle exist in the light detection region, since the photon detection event always occurs at random, the expected value Eni in each measuring unit time ti may be set to:

$$Eni = Bg \quad (3)$$

Here, Bg is the time average value of the background light. Thus, by substituting the value of Expression (3) into Expression (1), the unit time occurrence probability Pni in each measuring unit time ti is computed in time series, and, further, the probability Pn that the actual detected photon count sequence would occur when the condition that no particle exist in the light detection region is assumed is computed with Expression (2).

On the other hand, in a case that a particle exists in the light detection region, since the position of the light detection region CV is moving, a particle will pass through the inside of the light detection region CV as schematically drawn in FIG. 4B. In this process, the intensity value of light emitted from the particle in the light detection region and detected or the reduction amount of the background light reduced when the particle exists in the inside of the light detection region is decreased as the position of the particle becomes more apart from the almost center of the light detection region as shown in FIG. 5C. Thus, the expected value Epi in each unit time ti when a particle exists in the light detection region is also shown as a bell shaped function in which the time is a variable. Here, supposing the bell shaped function is approximated by a Gauss function, the expected value Epi is given by:

[Exp. 3]

$$Epi = Q \cdot \exp\left(-\frac{(ti-tc)^2}{2W^2}\right) + Bg \quad (4)$$

Here, it is assumed that the Gauss function has the peak intensity Q in arbitrary time tc in an analysis window (for example, the center of the analysis window). Moreover, the full width at half maximum of the Gauss function of Expression (4) is equal to the time d/v for the light detection region with the moving speed v to pass through the full width at half maximum, d, of a distribution in the radius r direction of the light intensity value emitted from a particle in the light detection region and detected or the reduction amount of the background light reduced due to the existence of a particle in the inside of the light detection region as illustrated in FIG. 5C, and accordingly, from this condition, w is given by:

[Exp. 4]

$$w = \frac{1}{2\sqrt{2\ln 2}} \frac{d}{v} \quad (5)$$

In this regard, the full width at half maximum d of FIG. 3D can be determined from the optical system.

In the case that a particle to be observed is a light-emitting particle, supposing the total of the photon counts in an analysis window is consistent to the total of the expected value of Expression (4), the peak intensity Q in Expression (4) is given by:

[Exp. 5]

$$Q = \frac{\sum_{i=0}^{n}(Ci - Bg)}{w\sqrt{2\pi}} \quad (6)$$

On the other hand, in the case that a particle to be observed is a non-light-emitting particle, by setting that the expected value of the absolute value of the reduction amount of the photon count follows Expression (4), the peak intensity Q is given by:

[Exp. 6]

$$Q = \frac{\sum_{i=0}^{n}(Bg - Ci)}{w\sqrt{2\pi}} \quad (7)$$

Then, by substituting the value of Expression (4) to Expression (1), the unit time occurrence probability Ppi in each measuring unit time ti is computed in time series, and further, the probability Pp that the actual detected photon count sequence would occur when the condition that a particle exists in the inside of the light detection region is assumed is computed with Expression (2). Thus, when the occurrence probability Pp of the detected photon count sequence in assuming the condition that a particle exists exceeds with a certain degree beyond the occurrence probability Pn of the detected photon count sequence in assuming the condition that no particles exist, it is judged that the signal of a particle exits in this analysis window.

In this connection, in an embodiment, for the judgment of whether a signal of a particle exists in an analysis window or not, the odds ratio OR of the occurrence probability Pp and the occurrence probability Pn:

$$OR=Pp(1-Pn)/(1-Pp)Pn \quad (8)$$

may be computed, and when its magnitude exceeds beyond a predetermined value, the existence of a signal of a particle in an analysis window may be judged.

In the above-mentioned detection processes of a signal of a particle, preferably, the analysis window is set to have more than the time width taken for a single particle to pass through the inside of the light detection region. Supposing a light detection region of radius r is moving at a velocity v, the time width of an analysis window will be set to be longer than:

$$2r/v \quad (9)$$

Further, preferably, an analysis window may be set successively for every unit time on time series light intensity data. According to this setting, the occurrence probability Pp, the occurrence probability Pn and/or the odds ratio OR will be computed along with the time series light intensity data. However, in that case, since the operation amounts will increase, an analysis window may be set for every several unit times. Furthermore, the analysis window may be set by dividing time series light-intensity data by the time width of the analysis window. In this case, the analysis windows will be set without overlapping mutually.

In the case that an analysis window is set for every unit time, when one particle signal exists, the judgment of the existence of the signal of the particle continues in the successive analysis windows. Namely, the signal of one particle corresponds to one section in which the judgment of the existence of the signal of the particle continues. Accordingly, the counting of signals of particles can be attained by counting the number of the sections in which the judgment of the existence of the signal of the particle continues. Further, in the above-mentioned detection processes of a signal of a particle, the bin time is set to a time not more than the time taken for a single particle to pass through the inside of the light detection region (Expression 9). This is for capturing the signal during the passing of a single particle over two or more bin times to detect the pattern of a time variation of light intensity value during the passing of the single particle (If the bin time is longer than the time of Expression 9, the pattern of the time variation of the light intensity value during the passing of the single particle could not be caught.).

FIG. 6 shows processes of detecting a single particle signal using probabilities Pp, Pn that the above-mentioned detected photon count sequence occurs in the form of the flow chart. Referring to the drawing, first, after the generation of time series light intensity data, the computation of the intensity value of background light is performed on the time series light intensity data (step 310). The intensity value of the background light may be the average of the intensity values (photon counts) in a region where no particle signals exist in the time series light intensity data. Thus, in one way of computing the intensity value of the background light, the average of all the intensity values except data of a predetermined proportion (for example, 20%) in the higher side and data of a predetermined proportion (for example, 20%) in the lower side of the obtained time series light intensity data may be employed as the intensity value of the background light. This is because it is considered that the data of the predetermined proportion in the higher side of the light intensity values would correspond to light-emitting particle signals and the data of the predetermined proportion in the lower side of the light intensity values would correspond to non-light-emitting particle signals. In this connection, the intensity value of the background light may be the average of the light intensity values on time series light intensity data obtained using a sample solution containing no particles to be observed.

Next, in the process of the present embodiment, the setting of analysis windows is performed on the time series light intensity data (step 320). As already noted, the length of one analysis window may be determined in accordance with the size and the moving speed of the light detection region (See Expression (9)). Further, preferably, an analysis window may be set in time series for every bin time. However, in order to reduce computation amounts, an analysis window may be set for every several bin times, or, analysis windows may also be set without mutually overlapping.

Then, when the setting of the analysis windows has been done, in accordance with the principle explained above, an occurrence probability Pn of the light intensity value sequence or photon count sequence in the analysis window in assuming that no particles exist in the light detection region (step 130), and an occurrence probability Pp of the light intensity value sequence or photon count sequence in the analysis window in assuming that a particle exists in the light detection region (step 140) each are computed. In this connection, especially in the present invention, a signal of a light-emitting particle and a signal of a non-light-emitting particle may exist on one time series light intensity data. Thus, for the occurrence probability Pp in assuming that a particle exists in the light detection region, an occurrence probability $Pp^+$ in assuming that a light-emitting particle exists in the light detection region and an occurrence probability $Pp^-$ in assuming that a non-light-emitting particle exists in the light detection region are computed, respectively ($Pp^+$ is a probability computed by Expression (6), and $Pp^-$ is a probability computed by Expression (7).). Then, the computed occurrence probabilities $Pp^+$, $Pp^-$, and Pn are compared with one another, and it is judged whether or not a light-emitting particle or a non-light-emitting particle exists in an analysis window (step 150). In this judgment, the odds ratio of the occurrence probability $Pp^+$ or $Pp^-$ and the occurrence probability Pn may be computed (see Expression (8)), and it may be judged that a light-emitting particle exists when the odds ratio of a light-emitting particle is beyond a predetermined value while it may be judged that a non-light-emitting particle exists when the odds ratio of a non-light-emitting particle is beyond a predetermined value. In this regard, in computing an occurrence probability $Pp^+$, $Pp^-$ in assuming that a particle exists in the light detection region, the expected value of the intensity value may be set in assuming that the intensity peak exists in the center of an analysis window. Actually, in most cases, the peak of the signal of a particle does not exist in the center of an analysis window, and the values of the occurrence probabilities $Pp^+$ and $Pp^-$ decrease as the actual position of the peak of the signal of a particle becomes more apart from the center of the analysis window, but, its value is higher than the value of the occurrence probability Pn in assuming that no actual particle signals exist.

The computation of occurrence probabilities Pp, Pn in an analysis window and the detection of a particle signal in the processes of the above-mentioned steps 130-150 may be conducted in all analysis windows set on light intensity data (step 160).

(iii) Determination of a Particle Concentration

Furthermore, by counting the number of signals of detected single particles, the determination of the number of particles may be done (counting of particles). Also, when the volume of the whole region which the light detection region has passed through is computed in an arbitrary way, the number density or concentration of a single particle in the sample solution can be determined from its volume value and the number of particles (Step 170).

Although the whole volume of the region which the light detection region has passed through may be theoretically computed based upon the excitation light or detected light wavelength the numerical aperture of lenses and the adjustment conditions of the optical system, it may be experimentally determined, for instance, from the number of particles, which have been detected by conducting the light intensity measurement, the detection of particles and the counting thereof with a solution having a known particle concentration (reference solution) under the same condition as that for the measurement of a sample solution to be tested, and the concentration of the particle in the reference solution. Concretely, for example, supposing the number of detected single particles is N in a reference solution of the particle concentration (number density) C, the whole volume Vt of the region the light detection region has passed through is given by:

$$Vt = N/C \quad (10).$$

Alternatively, the plurality of solutions of different single particle concentrations are prepared as reference solutions and the measurement is performed for each of the solutions, and then, the average value of the computed Vt is determined as the whole volume Vt of the region which the light detection region has passed through. Then, when Vt is given, the particle concentration c of the sample solution, whose counting result of the single particles is n, is given by:

$$c = n/Vt \quad (11)$$

In this regard, the volume of the light detection region and the volume of the whole region which the light detection region has passed through may be given by an arbitrary method, for instance, using FCS and FIDA, instead of the above-mentioned method. Further, in the device of this embodiment, there may be previously memorized in a storage apparatus of the computer the information on the relations (Expression (10)) between concentrations C and particle numbers N of various standard particles for assumed moving patterns of the light detection region, so that a user of the device can appropriately use the memorized information on the relation in conducting an optical analysis.

Accordingly, in the scanning molecule counting method in which a sample solution is scanned with the light detection region and particles are detected individually, the counting of particles in the sample solution, the determination of concentration, etc. can be achieved according to the above-mentioned procedures. Especially in the case of the present invention, light-emitting particles and non-light-emitting particles can be counted separately and the respective particle concentrations can be determined, and thereby, the determination of the concentration for each kind of particle can be achieved.

(4) Single Particle Detection Process of Detecting a Fixed Number of Signals

In the above-mentioned single particle detection process, after performing light measurement for a certain set time, signals of single particles are detected on the obtained light intensity data. In that case, when the particle concentration in a sample solution is unknown, the light intensity is measured for a certain fixed measuring time and the measuring time will be set long enough for the sake of a low particle concentration. On the other hand, when the particle concentration in a sample solution is high, the light intensity measurement will be continued more than a time necessary to determine a characteristic, such as a concentration, at the allowable or satisfactory accuracy. Moreover, in a case that the particle concentration in a sample solution is lower than a concentration which the experimenter has assumed and the set measuring time is insufficient, the error of the result would become large. Then, for a further alternative manner of the single particle detection process, the light intensity measurement with moving a light detection region and the detection of a signal of a single particle may be repeated until the number of signals reaches a predetermined number; the time taken for the number of signals to reach the predetermined number may be measured; and the particle concentration may be determined based on the time taken for the number of the signals of the single particles to reach the predetermined number. According to this structure, for a sample solution of a high particle concentration, the time taken for the light intensity measurement can be shortened, while for a sample solution of a low particle concentration, it becomes possible to continue the light intensity measurement until the particle count which attains the accuracy required for a result (namely, particle concentration) is obtained. And, by setting the predetermined number to be reached by the number of signals of single particles to the particle count which achieves the accuracy required for a result, the particle count which achieves the accuracy required for the result will be reflected in the time taken for the number of signals of single particles to reach the predetermined number, and thus, it is expected that the concentration value of the particles determined based on that time has the allowable or satisfactory accuracy.

(i) Basic Principle

A particle concentration value and a time taken for the number of signals to reach a predetermined number are associated with one another as follows: In a case that a light detection region is moved at a scanning speed u for time τ in a sample solution having a certain particle concentration C, assuming that the cross sectional area of the light detection region is S, the number X of detected signals is:

$$X = CSu\tau a\, N_A \quad (12)$$

where $N_A$ is the Avogadro's number. Thus, supposing it takes a time T for the number of the signals to reach the predetermined number XE, the light-emitting particle concentration C is given as a function of the time T by:

$$C = XE/(STuN_A) \quad (13)$$

In this regard, based on the time T, taken for the number of the signals to reach the predetermined number XE, and the number XE of the detected particles, a detection rate V of the particles per unit time is given by:

$$V = XE/T \quad (14),$$

and therefore, the particle concentration C is represented by:

$$C = V/(SuN_A) \quad (15)$$

In this Expression (15), the particle concentration C is proportional to the detection rate V in the first-order so that the correspondence relation between the particle concentration C and the detection rate V is intelligible, and therefore, in an actual experiment, the particle concentration C may be determined using the detection rate V.

(ii) Processing Operation Procedure

The single particle detection process for detecting a fixed number of signals may be performed, for example, by the procedures shown in the flow chart of FIG. 7. In the example of this drawing, briefly, a series of processes: the moving of the position of a light detection region, the detection of the light from the light detection region, the detection of signals of single particles and the counting of the detected particle signals are repetitively performed in every analytical time interval t (a predetermined time interval) until the detected particle count X reaches the end particle count XE (a predetermined number to which the number of single particle should reach). In this regard, it should be understood that a series of processes and structures described below are realized by the processing operations of the computer 18.

(a) Initial Setting

Referring to FIG. 7, in the operation processes, concretely, first, after dispensing a sample solution into the well(s) 10 of the micro plate 9 and putting it on the stage of the microscope, when a user inputs to the computer 18 a command of staring processes of a light intensity measurement and detecting and counting particles, the computer 18 performs, as the initial setting, the setting of the end particle count XE (step 10) and the setting of the analytical time interval t (step 20). The end particle count XE and the analytical time interval t may be arbitrarily set by the user. In order to achieve an accuracy requested in a result value of a particle concentration, the end particle count XE can be appropriately determined with reference to a result of a preliminary experiment using a solution having a known particle concentration. For the analytical time interval t, an arbitrary time interval enough shorter than the period until the number of particles (X) reaches the end particle count (XE) after starting the process may be appropriately set, considering the processing speed, etc. in the device 1. Further, for each of the end particle count XE and analytical time interval t, a value, determined beforehand with reference to a result of a preliminary experiment using a solution having a known particle concentration, may be memorized in the device 1 so that the memorized value can be used automatically or by a user's choice.

(b) Detection of the Number of Particles

When the setting of the end particle count XE and analytical time interval t has been made, the light intensity measuring process, the detection of signals of particles from measured light intensity data and detection of the number of particles x (step 30) in the analytical time interval t according to the scanning molecule counting method; and a process of accumulating the number of the particles x detected in step 30 and computing the total number X(tn) of the particles (step 40) are repetitively performed every analytical time interval t until the total number X(tn) of the particles reaches the end particle count XE (step 50) as described below. In this regard, prior to the repetitive execution of processes of steps 30-50, the starting time Ts of a series of processes may be memorized (step 25).

The process of the light detection and particle count detection in step 30 may be the same as in the process shown in FIG. 3 or FIG. 6. Briefly, the light intensity measurement is conducted for the analytical time interval t with moving the position of the light detection region within the sample solution (scanning the inside of the sample solution), and then, in the time series light intensity data obtained in the analytical time interval t, the detection of a signal indicating the existence of a single particle and the counting of the detected number are performed in the computer 18 by the processes according to programs memorized in a storage device.

Thus, when the number of particles x in the time series light intensity data in the analytical time interval t is detected, the total number $X(t_n)$ of the detected particles is computed with $$X(t_n)=X(t_{n-1})+x \quad (16)$$

(FIG. 7—step 40). Here, $X(t_{n-1})$ is the total number of the particles detected till the last analytical time interval t, and its initial value is 0. And, steps 30-40 are repeated every analytical time interval t until the total number of the detected particles X(tn) reaches the end particle count XE, namely, $$X(t_n) \geq XE \quad (17)$$

is established (step 50). Then, during the repeating of steps 30-50, when Expression (17) is established, the processes of the light intensity measurement of the sample solution and the detecting and counting of the particles are ended. When the repetitive operations of steps 30-50 are completed, the end time TE may be memorized (step 60).

(c) Indication of the Number of Particle and the Measurement End Time

By the way, in the period of the repetitive execution of steps 30-50 in every analytical time interval t (until Expression (17) is established), the total number of the detected particles $X(t_n)$ and/or the measurement end time TE or the measurement remaining time Tr may be indicated on a display, such as a monitor, etc. of the computer 18. According to this structure, it is advantageous in that a user can predict when an executed measurement is ended by seeing those indications.

For carrying out an indication as described above, when Expression (17) is not established in the judgment of step 50 of FIG. 7, the respective processes shown in dotted line in the drawing are executed. Concretely, first, the newest total number of the detected particle X(tn) computed in step 40 is indicated on the display (step 52). In this connection, when the repetitive executions of steps 30-50 have been already executed, the value of the total number X(tn) of the detected particles so far is updated. Subsequently, in order to compute the measurement end time TE or the measurement remaining time Tr, the detection rate v of the particle after the start of the processes of step 30-50 is computed (step 54). The detection rate v of the particle till the present may be given by:

$$v=X(t_n)/(Tp-Ts) \quad (18)$$

Here, Tp is the present time. Thus, using the detection rate v of the particle, the measurement remaining time Tr (time to the end of the processes of steps 30-50) is estimated as:

$$Tr=(XE-X(t_n))/v \quad (19)$$

Moreover, the measurement end time TE (time of the end of the processes of steps 30-50) is estimated as:

$$TE=Tp+Tr \quad (20)$$

(Step 56). Then, the estimated measurement end time TE or the measurement remaining time Tr is indicated on the display (step 58). In this connection, when the repetitive executions of steps 30-50 have been already executed, the already indicated values are updated. Further, when $X(t_n)=0$, it may be indicated that Tr and TE are unknown without calculating Expression (18) or (19).

By the way, as already noted, the above-mentioned processes of steps 30-50 in FIG. 7 are repeated every analytical time interval t. In this respect, the light intensity measurement of step 100 of FIG. 3 or FIG. 6 may be continuously performed from the start of measurement to its end even during the execution of the signal processing steps other than step 100. Namely, in the processes of the light detection and particle count detection, when the light intensity measurement for the analytical time interval t of one cycle is completed, the light intensity measurement in the analytical time interval t of the following cycle is performed continuously, and simultaneously, the processes of the detecting and counting of signals of particles from the light intensity data acquired in the analytical time interval t of the completed cycle are performed in the computer 18. Thereby, the detecting and counting of particles will be achieved in real time.

(d) Analysis, Such as Concentration Computation, Etc.

Then, when the number of particles reaches the end particle count, an analysis, such as a concentration computation, etc., may be performed using the time T (=TE−Ts) until the number of particles reaches the end particle count or other information which can be obtained from the detected signal(s) of the light-emitting particle(s) (step 70). As already noted, for a particle concentration, a particle detection rate V is computed with Expression (12) from the time T to reach the end particle count and the end particle count XE, and the particle concentration is determined from the particle detection rate V, using the relation of Expression (13).

In this regard, although the cross sectional area S of the passing region of the light detection region in Expression (12)-(15) may be computed theoretically based on the wavelength of excitation light or detected light, the numerical aperture of a lens and the adjustment condition of the optical system, the cross sectional area S may be determined experimentally, for example, from the number of particles, detected by performing the light intensity measurement, the detecting and counting of particles as explained above for a solution having a known particle concentration (a control solution) under the same conditions as the measurement of a sample solution to be tested, and the particle concentration of the control solution. Concretely, for example, for a control solution having a particle concentration C, supposing the number of detected particles in a light intensity measurement performed at the moving speed uo for a certain time τo is N, the cross sectional area S of the passing region of the light detection region is given by:

$$S=N/(C \cdot N_A \cdot uo \cdot \tau o) \qquad (21)$$

Furthermore, by preparing the plurality of solutions of different particle concentrations as control solutions and performing measurements for the respective solutions, the average of computed Ss may be employed as the cross sectional area S of the light detection region.

In order to verify the validity of the present invention explained above, the experiments described below were conducted. In this regard, it should be understood that the following embodiments illustrate the validity of the present invention only, not intended to limit the scope of the present invention.

Embodiment 1

It was verified that, in time series light intensity data obtained in the light measurement in accordance with the scanning molecule counting method of the present invention, a signal indicating the existence of a light-emitting particle and a signal indicating the existence of a non-light-emitting particle were detectable while being discriminated from one another.

For sample solutions, there were prepared solutions obtained by dispersing, into a 20% polyethylene glycol solution containing 3.25 nM of fluorescent dye: ATTO488, 2 fM of non-fluorescent beads (CP-40-10: spherotec (D:4000 nm)) as non-light-emitting particles, 2 fM of fluorescent beads (FP-4052-2: spherotec (D:4000 nm)) as light-emitting particles; and 1 fM of the fluorescent beads and 1 fM of the non-fluorescent beads, respectively. In the light measurement, a single molecule fluorescence measuring apparatus MF20 (Olympus Corporation), equipped with the optical system of a confocal fluorescence microscope and a photon counting system, was used, and time series light intensity data (photon count data) were acquired for each of the above-mentioned sample solutions in accordance with the manner explained in the above-mentioned "(2) Measurement of Light Intensity of a Sample Solution". In that time, for the excitation light, a 50 µW laser light of 488 nm was used and the light of 510-560 nm wavelength band was measured with bandpass optical filter 535BP, and thereby the time series photon count data was generated. In this regard, the diameter of the confocal volume was set to about 4 µm. The moving speed of the position of the light detection region in the sample solution was set to 9000 rpm (67.5 mm/second); BIN TIME was set to 50 µseconds and the measurements for 100 seconds were performed three times for each of the solutions.

The detection of single particle signals was performed in the manner of the individual detection of a single particle signal based on occurrence probabilities of light intensity variation explained in conjunction with FIG. 6. FIG. 8A shows a part of obtained time series light intensity data; FIG. 8B shows the odds ratio of occurrence probabilities in assuming that a non-light-emitting particle exists; and FIG. 8C shows the odds ratio in assuming that a light-emitting particle exists. As understood from the drawings, there were observed in FIG. 8A a light intensity reduction which is considered to correspond to the passing of a non-light-emitting particle (α) and a light intensity increase which is considered to correspond to the passing of a light-emitting particle (β), and consistent with those, the respective odds ratios increased. In the observation of the whole time series light intensity data, there were observed signals of non-light-emitting particles with the peak intensity of −87%−−2% relative to the background light and signals of light-emitting particles with the peak intensity of 8%-720% relative to the background light.

FIG. 9 shows average values (bar graphs) and standard deviations (error bar) of the numbers of signals of light-emitting particles (convex) and the number of signals of non-light-emitting particles (concave), detected in the above-mentioned processes, for the solution containing no particles (0:0); the solution containing only non-light-emitting particles (2:0); the solution containing only light-emitting particles (0:2); and the solution containing light-emitting particles and non-light-emitting particles (1:1), respectively. As understood from the drawing, there were detected, respectively, signals of light-emitting particles and signals of non-light-emitting particles of the numbers consistent with the ratio of the particles contained in the respective solutions. This shows that, in a case that a light-emitting particle and a non-light-emitting particle are included in the same sample solution, the light-emitting particle and non-light-emitting particle in the sample solution are detectable while being discriminated between one another, respectively, in accordance with the optical analysis technique of the present invention, that is, conducting the scanning molecule counting method in the presence of adequate background light. In addition, it was shown that the estimation of the contents of the respective particles is possible.

Thus, as understood from the results of the above-mentioned embodiments, according to the scanning molecule counting method following the teachings of the present invention, the detection of a light-emitting particle and a non-light-emitting particle dispersed in a sample solution and the acquisition of information about their concentrations become possible for each kind of the particles. Especially since, in the present invention, the signal of a single particle is detected individually, the detection of a particle is possible even when the particle concentration in a sample solution is in a concentration range lower than that required in optical analysis techniques, such as FCS, and this feature will be advantageous in conducting an analysis for rare or expensive sample, often used in the fields of medical and/or biological researches and developments of Medicine.

The invention claimed is:

1. A single particle detection device which detects single particles dispersed and moving at random in a sample solution using an optical system of a confocal microscope or a multiphoton microscope, comprising:
   a light detection region mover which moves a position of a light detection region of the optical system in the sample solution;
   a light detector which detects light from the light detection region; and
   a signal processor which generates time series light intensity data of the light from the light detection region detected with the light detector during moving the position of the light detection region in the sample solution and detects a signal indicating an existence of each single particle individually in the time series light intensity data;
   wherein the light from the light detection region detected by the light detector includes substantially constant background light; the single particles include a first single particle having an emitting light intensity higher than the background light and a second single particle having an emitting light intensity lower than the background light; the signal of the first single particle is an increase of the light intensity detected by the light detector occurring when the first single particle enters into the light detection region; and the signal of the second single particle is a reduction of the light intensity detected by the light detector occurring when the second single particle enters into the light detection region.

2. The device of claim 1, wherein the signal processor counts numbers of the individually detected signals indicating existences of the first and second particles separately to count numbers of the first and second single particles detected during the moving of the position of the light detection region.

3. The device of claim 1, wherein the emitted light intensity emitted from the first single particle per unit volume is higher than the background light intensity emitted from the inside of the light detection region per unit volume; and the emitted light intensity emitted from the second single particle per unit volume is lower than the background light intensity emitted from the inside of the light detection region per unit volume.

4. The device of claim 1, wherein the background light is fluorescence, phosphorescence, chemiluminescence, bioluminescence or scattered light owing to substance dispersed in the sample solution, or illumination light.

5. A single particle detection method of detecting single particles dispersed and moving at random in a sample solution using an optical system of a confocal microscope or a multiphoton microscope, comprising steps of:
   moving a position of a light detection region of the optical system in the sample solution;
   detecting light from the light detection region during moving the position of the light detection region in the sample solution, and generating time series light intensity data; and
   detecting in the time series light intensity data individually a signal indicating an existence of each single particle;
   wherein the detected light from the light detection region includes substantially constant background light; the single particles include a first single particle having an emitting light intensity higher than the background light and a second single particle having an emitting light intensity lower than the background light; the signal of the first single particle is an increase of the light intensity detected by the light detector occurring when the first single particle enters into the light detection region; and the signal of the second single particle is a reduction of the light intensity detected by the light detector occurring when the second single particle enters into the light detection region.

6. The method of claim 5, further comprising a step of counting numbers of the individually detected signals indicating existences of the first and second particles separately to count the numbers of the first and second single particles detected during the moving of the position of the light detection region.

7. The method of claim 5, wherein the emitted light intensity emitted from the first single particle per unit volume is higher than the background light intensity emitted from the inside of the light detection region per unit volume; and the emitted light intensity emitted from the second single particle per unit volume is lower than the background light intensity emitted from the inside of the light detection region per unit volume.

8. The method of claim 5, wherein the background light is fluorescence, phosphorescence, chemiluminescence, bioluminescence or scattered light owing to substance dispersed in the sample solution, or illumination light.

9. A non-transitory computer readable storage device having a computer program product including programmed instructions for optical analysis of detecting light from single particles dispersed and moving at random in a sample solution using an optical system of a confocal microscope or a multiphoton microscope, said programmed instructions causing a computer to perform steps comprising:
   moving a position of a light detection region of the optical system in the sample solution;
   detecting light from the light detection region during moving the position of the light detection region in the sample solution, and generating time series light intensity data; and
   detecting in the time series light intensity data individually a signal indicating an existence of each single particle;
   wherein the detected light from the light detection region includes substantially constant background light; the single particles include a first single particle having an emitting light intensity higher than the background light and a second single particle having an emitting light intensity lower than the background light; the signal of the first single particle is an increase of the light intensity detected by the light detector occurring when the first single particle enters into the light detection region; and the signal of the second single particle is a reduction of the light intensity detected by the light detector occurring when the second single particle enters into the light detection region.

10. The non-transitory computer readable storage device of claim 9, further comprising a step of counting numbers of the individually detected signals indicating existences of the first and second particles separately to count the numbers of the first and second single particles detected during the moving of the position of the light detection region.

11. The non-transitory computer readable storage device of claim 10, wherein the emitted light intensity emitted from the first single particle per unit volume is higher than the background light intensity emitted from the inside of the light detection region per unit volume; and the emitted light intensity emitted from the second single particle per unit volume is lower than the background light intensity emitted from the inside of the light detection region per unit volume.

12. The non-transitory computer readable storage device of claim 9, wherein the background light is fluorescence, phosphorescence, chemiluminescence, bioluminescence or scattered light owing to substance dispersed in the sample solution, or illumination light.

* * * * *